US006538037B2

(12) United States Patent
Bishop et al.

(10) Patent No.: US 6,538,037 B2
(45) Date of Patent: Mar. 25, 2003

(54) METHODS FOR PREPARATION AND USE OF 1α,24(S)-DIHYDROXYVITAMIN D$_2$

(75) Inventors: Charles W. Bishop; Joyce C. Knutson; Stephen Strugnell; Richard B. Mazess, all of Madison, WI (US)

(73) Assignee: Bone Care International, Inc., Madison, WI (US)

(*) Notice: Subject to any disclaimer, the term of this patent is extended or adjusted under 35 U.S.C. 154(b) by 4 days.

(21) Appl. No.: 09/891,963

(22) Filed: Jun. 26, 2001

(65) Prior Publication Data

US 2002/0032179 A1 Mar. 14, 2002

Related U.S. Application Data

(63) Continuation-in-part of application No. 09/211,991, filed on Dec. 14, 1998, now Pat. No. 6,251,883, which is a continuation-in-part of application No. 08/515,801, filed on Aug. 16, 1995, now abandoned, which is a continuation of application No. 08/275,641, filed on Jul. 14, 1994, now abandoned, which is a continuation of application No. 07/940,246, filed on Aug. 28, 1992, now abandoned, which is a continuation-in-part of application No. 07/637,867, filed on Jan. 8, 1991, now abandoned, and a continuation-in-part of application No. PCT/US92/00313, filed on Jan. 7, 1992.

(51) Int. Cl.$^7$ ............................................. A61K 31/045

(52) U.S. Cl. ..................................................... 514/729

(58) Field of Search ........................................ 514/729

(56) References Cited

U.S. PATENT DOCUMENTS

| | | | |
|---|---|---|---|
| 3,880,894 A | 4/1975 | DeLuca et al. | 514/335 |
| 4,022,891 A | 5/1977 | Takeshita et al. | 514/729 |
| 4,159,326 A | 6/1979 | Barton et al. | 514/331 |
| 4,195,027 A | 3/1980 | DeLuca et al. | 514/331 |
| 4,338,250 A | 7/1982 | DeLuca et al. | 514/331 |
| 4,391,802 A | 7/1983 | Suda et al. | 424/236 |
| 4,554,106 A | 11/1985 | DeLuca et al. | 260/397.2 |
| 4,670,190 A | 6/1987 | Hesse et al. | 514/729 |
| 4,698,328 A | 10/1987 | Neer et al. | 514/12 |
| 4,719,204 A | 1/1988 | DeLuca et al. | 514/325 |
| 4,973,584 A | 11/1990 | DeLuca et al. | 514/329 |
| 5,098,899 A | 3/1992 | Gilbert et al. | 514/729 |
| 5,104,864 A | 4/1992 | DeLuca et al. | 514/321 |
| 5,260,290 A | 11/1993 | DeLuca et al. | 514/321 |
| 5,486,636 A | 1/1996 | DeLuca et al. | 556/443 |
| 5,488,120 A | 1/1996 | Knutson et al. | 552/653 |
| 5,532,391 A | 7/1996 | DeLuca et al. | 514/329 |
| 5,763,428 A | 6/1998 | Knutson et al. | 514/167 |
| 5,763,429 A | 6/1998 | Bishop et al. | 514/168 |
| 5,786,348 A | 7/1998 | Bishop et al. | 514/167 |
| 5,789,397 A | 8/1998 | Bishop et al | 514/167 |
| 5,798,345 A | 8/1998 | Knutson et al. | 514/167 |
| 5,801,164 A | 9/1998 | Knutson et al. | 514/167 |
| 6,025,346 A | 2/2000 | Knutson et al. | 514/167 |
| 6,087,350 A | 7/2000 | Johnson et al. | 514/168 |
| 6,166,000 A | 12/2000 | Bishop et al. | 514/167 |
| 6,211,168 B1 | 4/2001 | Bishop et al. | 514/167 |

FOREIGN PATENT DOCUMENTS

| | | |
|---|---|---|
| WO | WO 92/05130 | 4/1992 |
| WO | WO 94/05630 | 3/1994 |
| WO | WO 96/40153 | 12/1996 |
| WO | WO 96/40154 | 12/1996 |
| WO | WO 97/23242 | 7/1997 |
| WO | WO 98/56387 | 12/1998 |
| WO | WO 98/56389 | 12/1998 |
| WO | WO 99/16451 | 4/1999 |
| WO | WO 99/49027 | 9/1999 |
| WO | WO 99/49870 | 10/1999 |
| WO | WO 00/03700 | 1/2000 |
| WO | WO 01/22974 | 4/2001 |
| WO | WO 01/64251 | 9/2001 |

OTHER PUBLICATIONS

Strugnell et al., Abstract to "1 alpha, 24(S)–dihydroxyvitamin D2: a biologically active product of 1 alpha–hydroxyvitamin D2 made in the human hepatoma, Hep3B", from Biochemical Journal, 310 (Pt 1), pp. 233–241, Aug. 15, 1995.*

Horst et al., . . . Biochem., vol. 32, No. 11, pp. 2060–2063, 1986.*

Miller et al., "The Human Prostatic Carcinoma Cell Line LNCaP Expresses Biologically Active, Specific Receptors for 1α,25–Dihydroxyvitamin D$_3^1$," 52 *Cancer Res.* (1992) 515–520.

Skowronski et al., "Actions Of Vitamin D$_3$ Analogs on Human Prostate Cancer Cell Lines: Comparison with 1,25–Dihydroxyvitamin D$_3$ " 136 *Endocrinology* (1995) 20–26.

Skowronski et al., "Vitamin D and Prostrate Cancer: 1,25 Dihydroxyvitamin D$_3$ Receptors and Actions in Human Prostate Cancer Cell Lines," 132 *Endocrinology* (1993) 1952–1960.

R. Belsey et al., *Rapid Communications*, pp. 554–557 (1971).

E. G. Bligh, *Canadian Journal of Biochemistry and Physiology*, vol. 37, pp. 911–917 (1959).

Harrison's Principles of Internal Medicine: Part Seven, "Disorders of Bone and Mineral Metabolism: Chap. 35," in E. Braunwald et al., Calcium, Phosphorus and Bone Metabolism: Calcium Regulating Hormones, McGraw–Hill, New York, pp. 1860–1865, 1992.

H. F. DuLuca et al., *Prog. Clin. Biol Res.*, vol. 259, pp. 41–55 (1988).

M.F. Holick et al., *J. Biol. Chem.*, vol. 248, pp. 6691–6696 (1973).

(List continued on next page.)

Primary Examiner—Dwayne C. Jones
(74) Attorney, Agent, or Firm—Michael Best & Friedrich LLP; Teresa J. Welch; Jeffrey D. Peterson

(57) ABSTRACT

A method of inhibiting the hyperproliferation of malignant or neoplastic cells, comprising treating the cells with an antiproliferative amount of 1α,24(S)-dihydroxyvitamin D$_2$. The method also includes the co-administration of cyotoxic angents with the 1α,24(S)-dihydroxyvitamin D$_2$.

82 Claims, 5 Drawing Sheets

OTHER PUBLICATIONS

B. W. Hollis, *Clin. Chem.*, vol. 32, No. 11, pp. 2060–2063 (1986).

R. L. Horst et al., *Biochem.*, vol. 29, pp. 578–582 (1990).

S. Ishizuka et al., *Steroids*, vol. 37, No. 1, pp. 33–42 (1981).

S. Ishizuka et al., *Steroids*, vol. 39, No. 1, pp. 53–62 (1982).

G. Jones, *Clin. Chem.*, vol. 24, No. 2. pp. 287–298 (1978).

G. Jones et al., *Biochemistry*, vol. 18, No. 6, pp. 1094–1101 (1979).

G. Jones et al., *Archives of Biochemistry and Biophysics*, vol. 202, No. 2, pp. 450–457 (1980).

H. E. Paaren et al, *J. Org. Chem.*, vol. 45. pp. 3253–3258 (1980).

J. G. Rheinwald et al., *Cell*, vol. 6. pp. 331–343 (1975).

H. L. Shieh et al., *Chem–Biol. Interact*, vol. 81, pp. 35–55 (1992).

S. Strugnell et al., *Biochemical Pharmacology*, vol. 40, pp. 333–341 (1990).

S. Tam et al., *Journal of Lipid Research*, vol. 29, pp. 1637–1642 (1988).

N. J. Koszewski et al., "Use of Fourier Transform H NMR in the Identification of Vitamin $D_2$ Metabolites", *Analytical Biochemistry*, vol. 162 (1987).

G. W. Engstrom et al. "Metabolism of Vitamin $D_2$ in Pig Liver Homogenates: Evidence for a Free Radical Reaction", *Archives of Biochemistry and Biophysics*, vol. 270, No. 2, pp. 432–440 (1989).

G. S. Reddy et al., "24,25,28–Trihydroxyvitamin $D_2$ and 24,25,26–Trihydroxyvitamin $D_2$: Novel Metabolites of Vitamin $D_2$", vol. 29, No. 4, pp. 943–949 (1990).

Calcium Regulation and Bone Metabolism Basic and Clinical Aspects, vol. 9 in R. L. Horst et al., *Quantitation and Biological Evaluation of the C–24 Hydroxylation Pathway of Vitamin $D_2$*, Excerpta Medica, Amsterdam–New York–Oxford, p. 598, 1987.

Beer, et al., "A Phase I Trial of Pulse Calcitriol in Patients with Refractory Malignancies," *Cancer*, vol. 91, No. 12 (Jun. 15, 2001) 2431–2439.

Beer, et al., "Weekly High–Dose Calcitriol and Docetaxel in Advanced Prostate Cancer," *Seminars in Oncology*, vol. 28, No. 4., Suppl 15 (Aug. 2001) 49–55.

Kim, Joonggon, "Synthesis in the Vitamin D Series. A Novel Route to Ring A Synthon and Vitamin D Analogs (Hydroxyvitamin D)," Thesis submitted at University of Illinois Chicago, Publication No. AAT 9335131, 1993.

* cited by examiner

Relative affinities of crystalline 1α,24-dihydroxyvitamin $D_2$,
powdered 1α,24-dihydroxyvitamin $D_2$ and
standard 1α,24-dihydroxyvitamin $D_2$ for the vitamin D receptor (VDR)

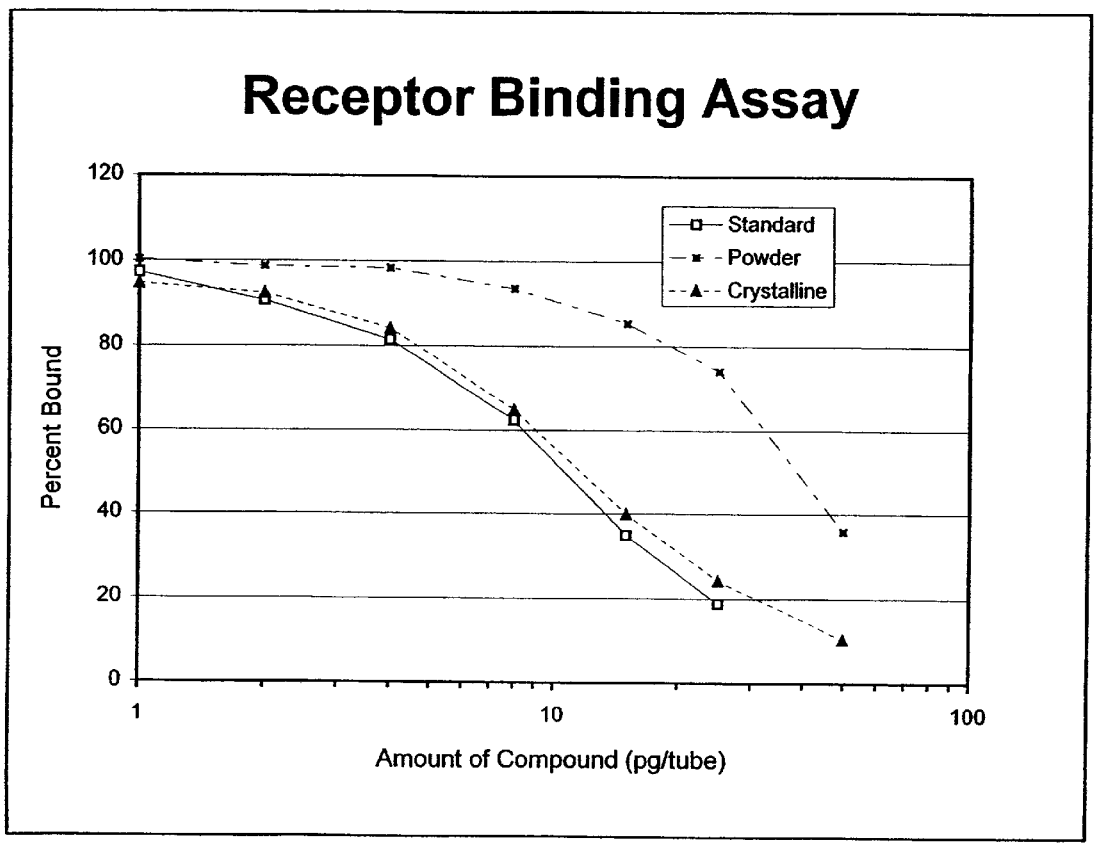

The relative affinities of crystalline 1α,24-dihydroxyvitamin $D_2$ (triangles), powdered 1α,24-dihydroxyvitamin $D_2$ (stars) and standard 1α,24-dihydroxyvitamin $D_3$ (squares) for the VDR using commercially available reagents of bovine thymus VDR and standard $^3$H-1α,25-dihydroxyvitamin $D_3$ solutions from INCstar (Stillwater, Minnesota).

FIGURE 5

METHODS FOR PREPARATION AND USE OF 1α,24(S)-DIHYDROXYVITAMIN $D_2$

CROSS-REFERENCE TO RELATED APPLICATIONS

This application is a continuation-in-part of U.S. application Ser. No. 09/211,991, filed Dec. 14, 1998, now U.S. Pat. No. 6,251,883, which is a continuation-in-part of U.S. application Ser. No. 08/515,801, filed Aug. 16, 1995, now abandoned, which is a continuation of U.S. application Ser. No. 08/275,641 filed Jul. 14, 1994, now abandoned, which is a continuation of U.S. application Ser. No. 07/940,246, filed Aug. 28, 1992, now abandoned, which is a continuation-in-part of U.S. application Ser. No. 07/637,867, filed Jan. 8, 1991, now abandoned, and International Application No. PCT/US92/00313, filed Jan. 7, 1992, and which designated the U.S.

STATEMENT REGARDING FEDERALLY SPONSORED RESEARCH OR DEVELOPMENT

Not Applicable

This invention relates to the hormonally active, natural metabolite 1α,24(S)-dihydroxyvitamin $D_2$ and to methods of preparing this metabolite and the nonbiological epimer 1α,24(R)-dihydroxyvitamin $D_2$. This invention also relates to a pharmaceutical composition which includes a pharmaceutically effective amount of 1α,24(S)-dihydroxyvitamin $D_2$, to a method of controlling abnormal calcium metabolism by administering a pharmaceutically effective amount of the compound, and to a method of treating hyperproliferative diseases by administering the compound.

Vitamin D and its active metabolites are known to be important in regulating calcium metabolism in animals and humans. The naturally occurring form of vitamin D in animals and humans is vitamin $D_3$. It has been shown that in animals, including humans, vitamin $D_3$ is activated by being hydroxylated in the $C_{25}$ position in the liver, followed by 1α-hydroxylation in the kidney to produce the hormone 1α,25-dihydroxyvitamin $D_3$ ["1α,25-$(OH)_2D_3$"]. See, U.S. Pat. No. 3,880,894. The major physiological pathway for catabolism of the vitamin $D_3$ metabolites, 25-hydroxyvitamin $D_3$ and 1α,25-$(OH)_2D_3$, is initiated by $C_{24}$-oxidation. Holick, M. F., Kleiner-Bossallier, A., Schnoes, H. K., Kasten, P. M., Boyle, I. T., and DeLuca, H. F., *J. Biol. Chem.*, 248, 6691–6696 (1973).

Vitamin $D_2$, on the other hand, is the major, naturally occurring form of vitamin D found in plants. Vitamin $D_2$ differs structurally from vitamin $D_3$ in that vitamin $D_2$ has a methyl group at $C_{24}$ and has a double bond between $C_{22}$ and $C_{23}$.

Shortly after their discovery, it seemed apparent that vitamin $D_3$ and vitamin $D_2$ had similar, if not equivalent, biological activity. It has also been commonly believed that the metabolism (i.e., the activation and catabolism) of vitamin $D_2$ was the same as for vitamin $D_3$. See, Harrison's Principles of Internal Medicine: Part Seven, "Disorders of Bone and Mineral Metabolism: Chap. 35," in E. Braunwald, K. J. Isselbacher, R. G. Petersdorf, J. D. Wilson, J. B. Martin and H. S. Fauci (eds.), *Calcium, Phosphorus and Bone Metabolism: Calcium Regulating Hormones*, McGraw-Hill, New York, pp. 1860–1865. In this regard, the active form of vitamin $D_2$ is believed to be 1α,25-dihydroxyvitamin $D_2$ ["1α,25-$(OH)_2D_2$"]. Further, 24-hydroxy derivatives of 25-hydroxyvitamin $D_2$ and 1α,25-$(OH)_2D_2$, i.e., 24,25-dihydroxyvitamin $D_2$ and 1α,24,25-trihydroxyvitamin $D_2$, are known, suggesting that catabolism of vitamin $D_2$, like vitamin $D_3$, proceeds through the same $C_{24}$ oxidation step. Jones, G., Rosenthal, D., Segev, D., Mazur, Y., Frolow, F., Halfon, Y., Robinavich, D. and Shakked, Z., *Biochemistry*, 18:1094–1101 (1979).

It has recently been found, however, that an active analogue of vitamin $D_2$, 1α-hydroxyvitamin $D_2$ ["1α-$(OH)D_2$"] has pharmacological properties distinctly different than those exhibited by its vitamin $D_3$ counterpart, 1α-hydroxyvitamin $D_3$ ["1α-$(OH)D_3$"]. U.S. Pat. No. 5,104,864 discloses that 1α-$(OH)D_2$ will reverse the loss of bone mass in human osteoporotic patients when administered at dosages of 2.0 μg/day or higher. Because of toxicity, dosage levels of 2.0 μg/day or greater are not safely obtained with 1α-$(OH)D_3$.

Such distinct pharmacological properties may be explained fully, or in part, by the present inventors' discovery that pharmacological dosages of 1α-$(OH)D_2$ administered to humans are metabolized in part to biologically active 1α,24(S)-dihydroxyvitamin $D_2$ ["1α,24(S)-$(OH)_2D_2$"]. As explained in more detail below, the hydroxylation at the carbon-24 position of the 1-hydroxylated vitamin $D_2$ molecule, represents an activation pathway peculiar to the vitamin $D_2$ molecule.

While 1α,24(S)-dihydroxyvitamin $D_3$ and 1α,24(R)-dihydroxyvitamin $D_3$ ["1α,24(R/S)-$(OH)_2D_3$"] have been chemically synthesized (U.S. Pat. No. 4,022,891) it has not been demonstrated that either is a natural compound found in biological systems. Furthermore, the present inventors have discovered that 1α,24(S)-$(OH)_2D_2$ has distinctly different biological activity from that exhibited by 1α,24(R/S)-$(OH)_2D_3$. For example, Ishizuka et al. have found that 1α,24(R)-$(OH)_2D_3$ binds the 1,25-$(OH)_2D_3$ receptor site more tightly than does 1,25-$(OH)_2D_3$ itself. Ishizuka, S., Bannai, K., Naruchi, T. and Hashimoto, Y., *Steroids*, 37:1, 33–42 (1981); Ishizuka, S., Bannai, K., Naruchi, T. and Hashimoto, Y., *Steroids*, 39:1,53–62 (1982). Using a similar assay, the present inventors have discovered that the 1α,24(S)-$(OH)_2D_2$ is two-fold less competitive in binding the 1,25-$(OH)_2D_3$ receptor site than is 1,25-$(OH)_2D_3$. The present inventors have also found that 1α,24(S)-$(OH)_2D_2$ shows a relatively poor binding affinity for the vitamin D serum binding protein which is evidence of a rather short half life indicative of low toxicity.

The present inventors have demonstrated the presence of circulating 1α,24(S)-$(OH)_2D_2$ in humans administered 1α-$(OH)D_2$. This indicates that in animals and man, vitamin $D_2$ is naturally metabolized to both 1α,25-$(OH)_2D_2$ and 1α,24(S)-$(OH)_2D_2$. The relative ratios of the two vitamin $D_2$ hormones appear to vary according to the precursor and the amount of precursor presented to the $C_{24}$ pathway. Thus, it appears that as dosages of 1α-$(OH)D_2$ are increased, the ratio of 1α,24(S)-$(OH)_2D_2$ to 1α,25-$(OH)_2D_2$ increases.

These results which are presented in more detail below, indicate that 1α,24(S)-$(OH)_2D_2$ has the desirable characteristic of high biological activity with low toxicity. The fact that 1α,24(S)-$(OH)_2D_2$ is a significant metabolite when pharmacological levels of 1α-$(OH)D_2$ are administered indicates that 1α,24(S)-$(OH)_2D_2$ may be mediating the desirable pharmacological effects of 1α-$(OH)D_2$ and is a useful therapeutic drug for treating various types of disorders involving calcium metabolism.

Extensive research during the past two decades has also established important biologic roles for vitamin D apart from its classic role in bone and mineral metabolism. Specific nuclear receptors for 1α,25-dihydroxyvitamin $D_3$, the hormonally active form of vitamin D, are present in cells from diverse organs not involved in calcium homeostasis. For example, specific, biologically active vitamin D receptors have been demonstrated in the human prostatic carcinoma cell line, LNCaP, (Miller et al., 52 *Cancer Res.* (1992) 515–520). Vitamin D receptors have also been described for many other neoplastic cells, e.g., carcinomas of the breast and of the colon.

It has been demonstrated that certain vitamin D compounds and analogues are potent antiproliferative and prodifferentiative agents. For example, U.S. Pat. No. 4,391,802 issued to Suda et al. discloses that 1α-hydroxyvitamin D compounds, specifically 1α,25-dihydroxyvitamin $D_3$ and 1α-hydroxyvitamin $D_3$, possess potent antileukemic activity by virtue of inducing the differentiation of malignant cells (specifically leukemia cells) to nonmalignant macrophages (monocytes), and are useful in the treatment of leukemia. Antiproliferative and differentiating actions of 1α,25-dihydroxyvitamin $D_3$ and other vitamin $D_3$ analogues have also been reported with respect to prostate cancer cell lines. More recently, an association between vitamin D receptor gene polymorphism and prostate cancer risk has been reported, suggesting that vitamin D receptors may have a role in the development, and possible treatment, of prostate cancer.

These previous studies have focused exclusively on vitamin $D_3$ compounds. Even though these compounds may be highly effective in promoting differentiation in malignant cells in culture, their practical use in differentiation therapy as anticancer agents is severely limited because of their equally high potency as agents affecting calcium metabolism. At the levels required in vivo for effective use as, for example, as antileukemic agents, these same compounds can induce markedly elevated and potentially dangerous blood calcium levels by virtue of their inherent calcemic activity. That is, the therapeutic use of 1α,25-dihydroxyvitamin $D_3$ and other vitamin $D_3$ analogues as anticancer agents is precluded, or severely limited, by their side effects which include hypercalcemia and hypercalciuria. This indicates a need for compounds with greater specific activity and selectivity of action, i.e., vitamin D compounds with antiproliferative and prodifferentiating effects but which have low calcemic activity. Such compounds are "hypocalcemic" vitamin D compounds. The need for such compounds is no greater than in the treatment of neoplastic and hyperproliferative diseases.

The present invention provides synthetic 1α,24(S)-dihydroxyvitamin $D_2$ [1α,24(S)-$(OH)_2D_2$] which is a biologically-produced active form of vitamin $D_2$. The biological form may also be referred to as 1α,24(S)-dihydroxy ergocalciferol and is represented by the structure given hereinafter. The biological form of the compound has potent biological activity and rapid systemic clearance, indicating low toxicity.

The invention also encompasses a novel method of producing 1α,24(S)-dihydroxyvitamin $D_2$ which entails using ergosterol as a starting material, forming 24-hydroxyvitamin $D_2$ and then, 1α-hydroxlyating the 24-hydroxy compounds and separating the 1α,24(S)-dihydroxyvitamin $D_2$ epimer from the 1α,24(R)-dihydroxyvitamin $D_2$ epimer. In the course of this synthesis, novel intermediates are also produced. The crystalline form of 1α,24(S)-dihydroxyvitamin $D_2$ has further been found to have surprising stability and better biological activity than a white powder form of the compound.

The compound of the invention is useful in the treatment of various diseases characterized by vitamin D deficiency and various bone depletive disorders, in particular, treatment without the concomitant incidence of hypercalcemia or hypercalciuria. The compound of the invention is advantageously used as an active ingredient of pharmaceutical compositions for vitamin D deficiency diseases, for reversing or preventing the loss of bone mass or bone mineral content in persons predisposed to developing such loss, and for stabilizing bone density in persons suffering from renal osteodystrophy.

The compound of the invention is also useful as a topical and oral agent for treatment of certain skin disorders. The compound of the invention is advantageously used as an active ingredient in e.g., topical compositions which may also include other agents capable of ameloriating skin disorders.

The compound of the invention is also beneficial as a antiproliferative and prodiffentiative agent in the treatment of cancers and other hyperproliferative diseases.

Other advantages and a better appreciation of the specific adaptations, compositional variations, and physical and chemical attributes of the present invention will be gained upon an examination of the following detailed description of the invention, taken in conjunction with the accompanying drawings.

BRIEF DESCRIPTION OF THE DRAWINGS

The present invention will hereinafter be described in conjunction with the appended drawings, wherein like designations refer to like elements throughout and in which:

FIG. 5 is a graph illustrating the relative binding affinities of crystalline 1α,24-$(OH)_2D_2$ and powdered 1α,24-$(OH)_2D_2$.

As used herein, the terms "biological activity", "biologically active", "bioactive", or "biopotent" are meant to refer to biochemical properties of compounds such as affecting metabolism, e.g., affecting serum calcium concentration, or binding to an appropriate receptor protein, e.g., binding to vitamin D receptor protein. The term "substantially pure" in reference to compounds or substances means a purity of at least 90%.

The term "active" or "activated" in reference to vitamin D refers to a vitamin D compound that is hydroxylated in at least one of the $C_1$, $C_{25}$ or $C_{24}$ positions.

In one of its aspects, the invention encompasses the biologically active compound of the formula (I):

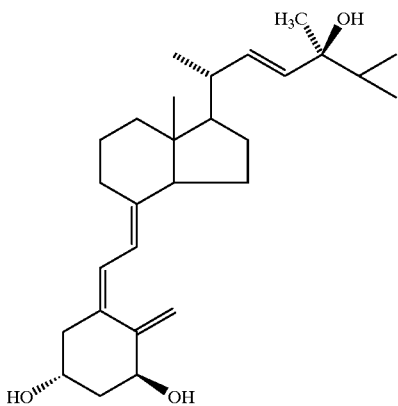

(I)

i.e., 1α,24(S)-dihydroxyvitamin $D_2$.

Figure 1:
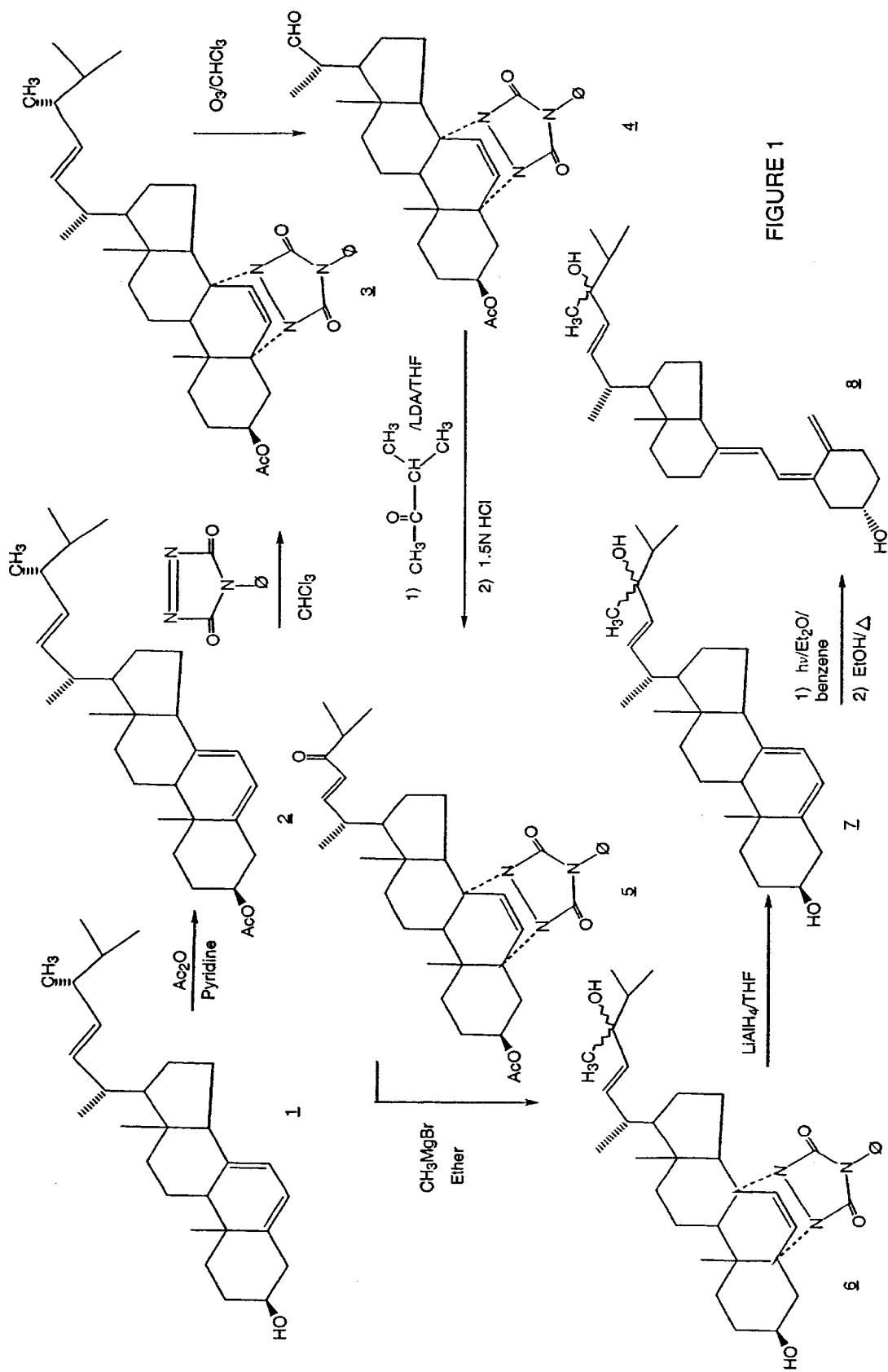
FIG. 1 illustrates preparative steps for the synthesis of 24-hydroxyvitamin $D_2$.
Figure 2:
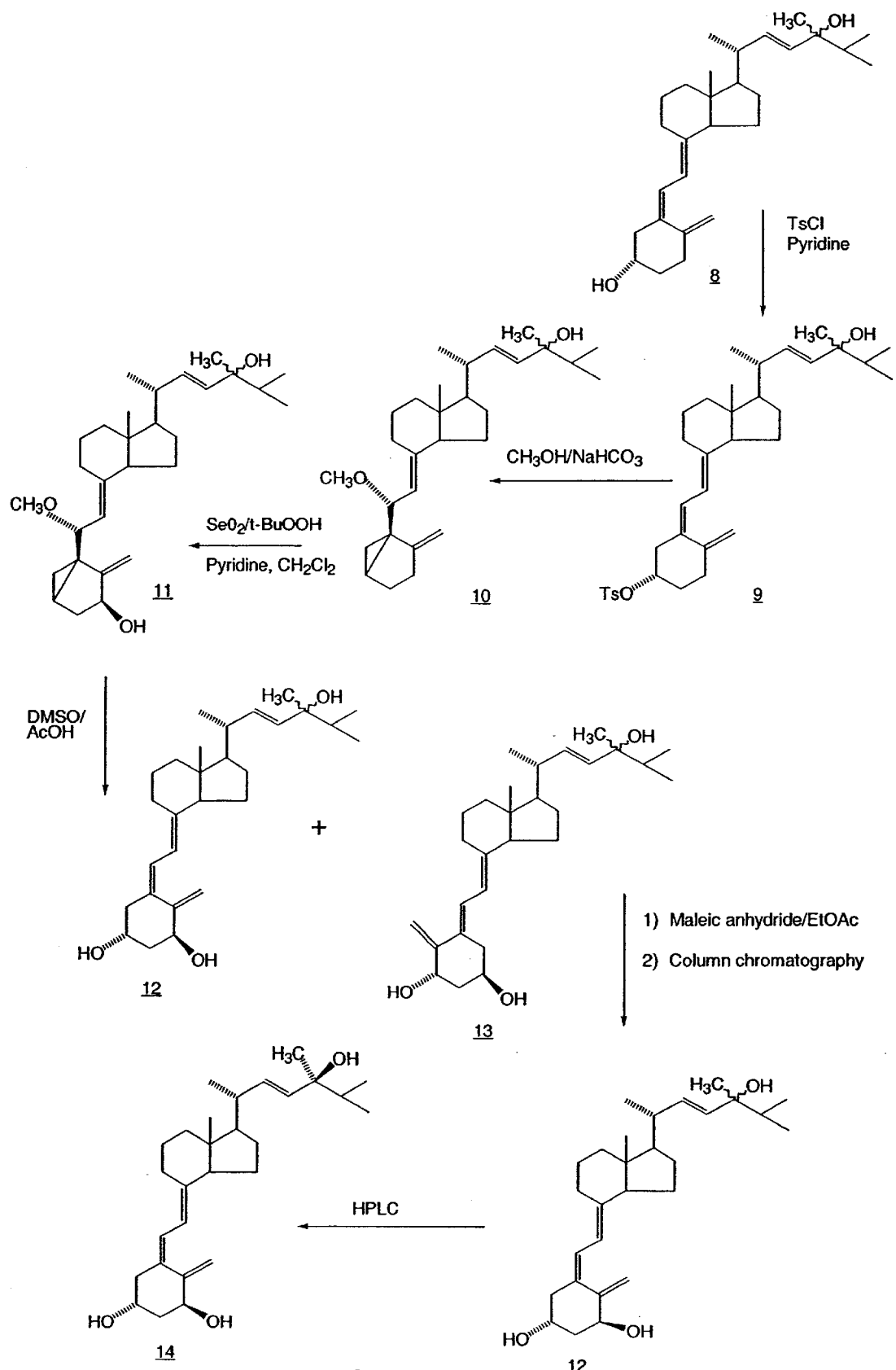
FIG. 2 illustrates preparative steps for the synthesis of 1α,24(S)-dihydroxyvitamin $D_2$ starting with 24-hydroxyvitamin $D_2$.

In another aspect, the invention involves the preparation of 1α,24(S)-dihydroxyvitamin $D_2$. Synthesis of 1α,24(S)-dihydroxyvitamin $D_2$ is accomplished according to the schema presented in FIGS. 1 and 2. Hereinafter when reference is made to a 24-hydroxy compound, unless specified, it will be presumed that the compound is an epimeric mixture of the R and S forms. As seen in FIG. 1, the synthesis uses ergosterol as the starting material. Ergosterol is converted to 24-hydroxyergosterol (5,7,22 ergostatriene-3β,24-diol (7)) by a five-step process. The 24-hydroxy ergosterol is then irradiated and thermally converted by methods well known in the art to yield 24-hydroxyvitamin $D_2$. As seen in FIG. 2, 24-hydroxyvitamin $D_2$ is then hydroxylated in a five-step process to yield 1α,24-dihydroxyvitamin $D_2$, using a procedure similar to that described by Paaren, et al., *J. Org. Chem.*, vol. 45, p. 3253 (1980), from which the epimers are separated.

Specifically, ergosterol is acetylated to form the 3β-acetate (2). An adduct (3) is then formed with the B-ring of the ergosterol structure by reaction of the 3β-acetate with a triazoline dione. The adduct (3) is then ozonated to truncate the side chain to form a C-21 aldehyde (4). The side chain is reestablished by reaction of the resulting aldehyde with the appropriate keto-compound to yield the 24-enone (5). The enone is then converted to the 24-methyl, 3β,24-dihydroxy adduct (6). This adduct is then reacted with a lithium aluminum hydride to deprotect the adduct and yield 24-hydroxy ergosterol (7). The 24-hydroxy ergosterol is then irradiated and thermally treated to form 24-hydroxyvitamin $D_2$. The 24-hydroxyvitamin $D_2$ is then tosylated to yield 3β-tosylate of the 24-hydroxyvitamin $D_2$. The tosylate is displaced by solvolysis to yield the 6-methoxy-24-hydroxy-3,5-cyclovitamin $D_2$. The cyclovitamin $D_2$ is subjected to allylic oxidation to form the 1α,24-dihydroxycyclovitamin derivative. The 1α,24-dihydroxycyclovitamin derivative is sequentially solvolyzed and subjected to a Diels-Alder type reaction which removes the 6-methoxy group and separates the 1α,24-dihydroxyvitamin $D_2$ (5,6 cis) from the 5,6 trans 1α,24-dihydroxyvitamin $D_2$.

The 1α,24-$(OH)_2D_2$ is subjected to reverse phase high pressure liquid chromatography to separate the two epimers and recover the epimeric form of the invention, 1α,24(S)-$(OH)_2D_2$.

The compound of the invention is applicable to various clinical and veterinary fields, and is particularly useful for the treatment of abnormal metabolism of calcium and phosphorus. Specifically, 1α,24(S)-dihydroxyvitamin $D_2$ is intended to be used, for example, to stimulate osteoblastic activity, as measured by serum levels of osteocalcin. Osteocalcin is one of the major proteins in the bone matrix. The 1α,24(S)-dihydroxyvitamin $D_2$ binds to the vitamin D serum binding protein more weakly than does 1,25-$(OH)_2D_3$, indicative of rapid clearance and low toxicity, which enhances its pharmaceutical properties.

In a further aspect, the invention entails a method of controlling calcium metabolism, such as for treating abnormal calcium metabolism caused, e.g., by liver failure, renal failure, gastrointestinal failure, etc. The 1α,24(S)-dihydroxyvitamin $D_2$ can be used to treat prophylactically or therapeutically vitamin D deficiency diseases and related diseases, for example, renal osteodystrophy, steatorrhea, anticonvulsant osteomalacia, hypophosphatemic vitamin D-resistant rickets, osteoporosis, including postmenopausal osteoporosis, senile osteoporosis, steroid-induced osteoporosis, and other disease states haracteristic of loss of bone mass, pseudodeficiency (vitamin D-dependent) rickets, utritional and malabsorptive rickets, osteomalacia and osteopenias secondary to hypoparathyroidism, post-surgical hypoparathyroidism, idiopathic hypothyroidism, pseudoparathyroidism, and alcoholism.

1α,24(S)-Dihydroxyvitamin $D_2$ is also of value for the treatment of hyperproliferative skin disorders such as psoriasis, eczema, lack of adequate skin firmness, dermal hydration, and sebum secretion.

The compound of formula (I) is further valuable for the treatment of breast and colon cancer, as well as other neoplasms such as pancreatic cancer, endometrial cancer, small cell and non-small cell cancer of the lung (including squamous, adneocarcinoma and large cell types), squamous cell cancer of the head and neck, bladder, ovarian and cervical cancers, myeloid and lymphocyltic leukemia, lymphoma, hepatic tumors, medullary thyroid carcinoma, multiple myeloma, melanoma, retinoblastoma, and sarcomas of the soft tissue and bone. The compound of formula (I) is administered in an amount that raises a serum level of vitamin D in the subject with a tumor or neoplasm to a supraphysiologic level for a sufficient period of time to induce differentiation or regression of the tumor or neoplasm without causing hypercalcemia. The compound of formula (I) is hypocalcemic and permits such supraphysiologic levels.

The compound of formula (I) can be given in daily dose or episodic does, e.g. once every 2–6 days or once a week. The dose on each day can be a single dose or divided as 2–4 subdoses which can be given an hour apart until the total dose is given.

In accordance with the present invention, when effective amounts of 1α,24(S)-dihydroxyvitamin $D_2$ are administered to patients with cancer or neoplasms, the proliferative activity of the abnormal neoplastic cells is inhibited or reduced, and cell differentiation is induced, promoted or enhanced, with significantly less hypercalcemia and hypercalciuria than is observed after the same amount of an activated vitamin $D_3$ (e.g., 1α-OH-$D_3$ or 1α,25-$(OH)_2D_3$) is administered in previously known formulations. Thus, the compound in accordance with the present invention has an improved therapeutic index relative to active forms of vitamin $D_3$ analogues.

For treatment for malignant conditions, the vitamin D in accordance with the present invention is suitably administered alone as an active ingredient in a pharmaceutical composition, or in combination with a cytotoxic agent.

In another aspect, the invention is a pharmaceutical composition which includes an vitamin D compound in accordance with the present invention; and an agent selected from the group consisting of (i) a cytotoxic agent, (ii) a bone agent, and combinations thereof; and a physiologically acceptable carrier.

Further, included within the scope of the present invention is a method of co-administration of the vitamin D of formula (I) with a cytotoxic or anticancer agent(s). Such agents suitably include antimetabolites (e.g., 5-fluoro-uracil, methotrexate, fludarabine), antimicrotubule agents (e.g., vincristine, vinblastine, taxanes such as paclitaxel, docetaxel), an alkylating agent (e.g., cyclophasphamide, melphalan, biochoroethylnitrosurea, hydroxyurea), platinum agents (e.g. cisplatin, carboplatin, oxaliplatin, JM-216, CI-973), anthracyclines (e.g., doxrubicin, daunorubicin), antibiolitics (e.g., mitomycin, idarubicin, adriamycin, daunomycin), topoisomerase inhibitors (e.g., etoposide, camptothecins) or any other antineoplastic agents (estramustine phosphate, prednimustine).

It is anticipated that the vitamin D of formula (I) used in combination with various anticancer drugs can give rise to a significantly enhanced cytotoxic effect on cancerous cells, thus providing an increased therapeutic effect. Specifically, as a significantly increased growth-inhibitory effect is obtained with the above disclosed combinations utilizing lower concentrations of the anticancer drugs compared to the treatment regimes in which the drugs are used alone, there is the potential to provide therapy wherein adverse side effects associated with the anticancer drugs are considerably reduced than normally observed with the anticancer drugs used alone in larger doses. Possible dose ranges of these co-administered anticancer agents are about 0.1 to 20 mg/kg/day.

The term "co-administration" is meant to refer to any administration route in which two or more agents are administered to a patient or subject. For example, the agents may be administered together, or before or after each other. The agents may be administered by different routes, e.g., one agent may be administered intravenously while the second agent is administered intramuscularly, intravenously or orally. The agents may be administered simultaneously or sequentially, as long as they are given in a manner sufficient to allow both agents to achieve effective concentrations in the body. The agents may also be in an admixture, as, for example, in a single tablet. In sequential administration, one agent may directly follow administration of the other or the agents may be given episodically, i.e., one can be given at one time followed by the other at a later time, typically within a week.

Also included within the scope of the present invention is the co-administration of effective dosages of the compound of formula (I) in conjunction with administration of hormones or other agents, e.g., estrogens, which are known to ameliorate bone diseases or disorders. For example, prostate cancer often metastasizes to bone, causing bone loss and associated pain. Such bone agents may include conjugated estrogens or their equivalents, calcitonin, bisphosphonates, calcium supplements, cobalamin, pertussis toxin and boron.

$1\alpha,24(S)$-dihydroxyvitamin $D_2$ is useful as an active compound in pharmaceutical compositions having reduced side effects and low toxicity as compared with the known analogs of active forms of vitamin $D_3$, when applied, for example, to diseases induced by abnormal metabolism of calcium or to hyperproliferative diseases or neoplasmic diseases. These pharmaceutical compositions constitute another aspect of the invention.

The pharmacologically active compound of this invention can be processed in accordance with conventional methods of pharmacy to produce medicinal agents for administration to patients, e.g., mammals including humans, entically, parentically or topically. For example, the $1\alpha,24(S)$-dihydroxyvitamin $D_2$ can be employed in admixtures with conventional excipients, e.g., pharmaceutically acceptable carrier substances suitable for enteral (e.g., oral), parenteral, or topical application which do not deleteriously react with the active compound.

Suitable pharmaceutically acceptable carriers include but are not limited to water, salt solutions, alcohols, gum arabic, vegetable oils (e.g., almond oil, corn oil, cottonseed oil, peanut oil, olive oil, coconut oil), mineral oil, fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring, flavoring and/or one or more other active compounds, for example, vitamin $D_3$ and its $1\alpha$-hydroxylated metabolites, conjugated estrogens or their equivalents, anti-estrogens, calcitonin, biphosphonates, calcium supplements, cobalamin, pertussis toxin and boron.

For parenteral application, particularly suitable are injectable, sterile solutions, preferably oily or aqueous solution, as well as suspensions, emulsions, or implants, including suppositories. Parenteral administration suitably includes subcutaneous, intramuscular, or intravenous injection, nasopharyngeal or mucosal absorption, or transdermal absorption. Where indicated, the compound in accordance with the present invention may be given by direct injection into the tumor, e.g., parathyroid adenoma, or by regional delivery, e.g., by intra-arterial delivery or delivery via the portal vein. Regional delivery is especially suitable for treatment of heptic cancer. Ampoules are convenient unit dosages.

For enteral application, particularly suitable are tablets, dragees, liquids, drops, suppositories, lozenges, powders, or capsules. A syrup, elixir, or the like can be used if a sweetened vehicle is desired.

For topical application, suitable nonsprayable viscous, semi-solid or solid forms can be employed which include a carrier compatible with topical application and having a dynamic viscosity preferably greater than water, for example, mineral oil, almond oil, self-emulsifying beeswax, vegetable oil, white soft paraffin, and propylene glycol. Suitable formulations include, but are not limited to, creams, ointments, lotions, solutions, suspensions, emulsions, powders, liniments, salves, aerosols, transdermal patches, etc., which are, if desired, sterilized or mixed with auxiliary agents, e.g., preservatives, stabilizers, demulsifiers, wetting agents, etc. A cream preparation in accordance with the present invention suitably includes, for example, mixture of water, almond oil, mineral oil and self-emulsifying beeswax; an ointment preparation suitably includes, for example, almond oil and white soft paraffin; and a lotion preparation suitably includes, for example, dry propylene glycol.

Topical preparations of the compound in accordance with the present invention useful for the treatment of skin disorders may also include epithelialization-inducing agents such as retinoids (e.g., vitamin A), chromanols such as vitamin E, β-agonists such as isoproterenol or cyclic adenosine monophosphate (cAMP), anti-inflammatory agents such as corticosteroids (e.g., hydrocortisone or its acetate, or dexamethasone) and keratoplastic agents such as coal tar or anthralin. Effective amounts of such agents are, for example, vitamin A about 0.003 to about 0.3% by weight of the composition; vitamin E about 0.1 to about 10%; isoproterenol about 0.1 to about 2%; cAMP about 0.1 to about 1%; hydrocortisone about 0.25 to about 5%; coal tar about 0.1 to about 20%; and anthralin about 0.05 to about 2%.

For rectal administration, the compound is formed into a pharmaceutical composition containing a suppository base such as cacao oil or other triglycerides. To prolong storage life, the composition advantageously includes an antioxidant such as ascorbic acid, butylated hydroxyanisole or hydroquinone.

For treatment of calcium metabolic disorders, oral administration of the pharmaceutical compositions of the present invention is preferred. Generally, the compound of this invention is dispensed by unit dosage form comprising about 0.5 μg to about 25 μg in a pharmaceutically acceptable carrier per unit dosage. The dosage of the compound according to this invention generally is about 0.01 to about 1.0 μg/kg/day, preferably about 0.04 to about 0.3 μg/kg/day. Oral dosing for the treatment of cancers and neoplasms and other hyperproliferative diseases generally is about 10 μg to 200 μg/day.

For topical treatment of skin disorders, the dosage of the compound of the present invention in a topical composition generally is about 0.01 μg to about 50 μg per gram of composition. For treatment of cancers, the dosage of $1\alpha,24$ (S)-(OH)$_2$D$_2$ in a locally applied composition generally is about 0.01 μg to 100 μg per gram composition.

As noted above, dosing of the compound in accordance with the present invention can also be done on an episodic basis, in which case higher doses can be used, generally about 20μg to about 200 μg given once every 2 to 7 days.

Those of ordinary skill in the art will readily optimize effective dosages and co-administration regimens as determined by good medical practice and the clinical condition of the individual patient. Regardless of the manner of administration, it will be appreciated that the actual preferred amounts of active compound in a specific case will vary according to the efficacy of the specific compound employed, the particular compositions formulated, the mode of application, and the particular site and organism being treated. For example, the specific dose for a particular patient depends on the age, body weight, general state of health and sex, on the diet, on the timing and mode of administration, on the rate of excretion, and on medicaments used in combination and the severity of the particular disorder to which the therapy is applied. Dosages for a given host can be determined using conventional considerations, e.g., by customary comparison of the differential activities of the subject compounds and of a known agent, such as by means of an appropriate conventional pharmacological protocol.

In a still further aspect, the compound of the present invention can also be advantageously used in veterinary compositions, for example, feed compositions for domestic animals to treat or prevent hypocalcemia. Generally, the compound of the present invention is dispensed in animal feed such that normal consumption of such feed provides the animal about 0.01 to about 1.0 μg/kg/day.

The following examples are to be construed as merely illustrative, and not limitative of the remainder of the disclosure in any way whatsoever. In the following examples proton nuclear magnetic resonance ($^1$H NMR) spectra were recorded with a Bruker AM—400(400 MHz) with aspect 3000 Computer in CDCl$_3$ solutions with CHCl$_3$ as an internal standard. Chemical shifts are reported in ppm. Ultraviolet spectra were recorded with a Hitachi U-2000 Spectrophotometer and are reported for ethanol solutions.

EXAMPLE 1

Generation, Purification and Identification of $1\alpha,24$ (?)-(OH)$_2$D$_2$ in Human Liver Cells Incubated with $1\alpha$-(OH)D$_2$ Substantially pure $1\alpha$-(OH)D$_2$ was obtained from Bone Care International, Inc. of Madison, Wis. The $1\alpha$-(OH)D$_2$ was cultured for 48 hours with cells derived from a human hepatoma, Hep 3B, in medium devoid of fetal calf serum using known methods in the art.

Lipid extracts of the combined medium and cells were generated by known methods in the art and were subjected to high pressure liquid chromatography (HPLC) on Zorbax-S1L developed with hexane/isopropano/methanol (91:7:2). The putative $1\alpha,24$(?)-(OH)$_2$D$_2$ metabolite eluted between the parent $1\alpha$-(OH)D$_2$ and standard $1\alpha,25$-(OH)$_2$D$_2$ (also obtained from Bone Care International, Inc. of Madison, Wis.). (As used herein, the term "$1\alpha,24$(?)-(OH)$_2$D$_2$" is meant to indicate that the epimeric form has not been identified.) The $1\alpha,24$(?)-(OH)$_2$D$_2$ was further purified by this HPLC system before the metabolite's identification was undertaken using mass spectrometry analysis.

The purified metabolite was more polar than the starting material, $1\alpha$-(OH)D$_2$ and thus was tentatively concluded to be a dihydroxyvitamin D$_2$ metabolite. This metabolite also possessed the vitamin D chromophore, indicating retention of the cis-triene system of vitamin D. Since the metabolite was derived from $1\alpha$-(OH)D$_2$, its structure was thus $1\alpha$,X-(OH)$_2$D$_2$ where "X" indicates the position of the second hydroxyl group.

The trimethylsilyl-derivative of the $1\alpha$,X-(OH)$_2$D$_2$ was prepared according to known methods in the art and mass spectrometry was performed on the TMS-derivative and the native compound. The TMS-derivative was analyzed by GC-MS, and the identification was mainly derived from interpretation of the fragmentation pattern of the pyrometabolite. The molecular ion possessed a m/z of 644 indicating a dihydroxyvitamin D$_2$ with addition of three TMS groups accounting for 216 units of additional mass. Since $1\alpha$-(OH)D$_2$ has 3β- and $1\alpha$-groups and the putative metabolite had one additional hydroxyl, all three hydroxyls were thus derivatized. Distinctive fragments were found at m/z 601, 511, 421, 331 representing loss of a 43 mass unit of fragment alone or in addition to one, two or three TMS groups of 90 units each. This pattern was most likely explained by cleavage of the C-24 to C-25 bond loss of C$_3$H$_7$ accounting for 43 mass units. This represents loss of the C$_{26}$–C$_{25}$–C$_{27}$ fragment. Furthermore, the mass spectrum lacked the m/z 131 fragment characteristic of all 25-hydroxylated vitamin D compounds.

The mass spectrum showed the m/z 513 fragment indicating loss of 131 mass units due to A-ring cleavage with loss of C$_2$–C$_3$–C$_4$ also characteristic of vitamin D compounds. The mass spectrum also contained m/z 143 which was probably derived from C-24 to C-23 cleavage and a loss of a methyl group. The unusual loss of 43 units indicating C$_{24}$–C$_{25}$ fragility coupled with the loss of a fragment due to C$_{23}$–C$_{24}$ cleavage indicated that the extra hydroxyl in $1\alpha$,X-(OH)$_2$D$_2$ was at carbon-24. Thus, the structure was identified as $1\alpha,24$(?)-(OH)$_2$D$_2$.

The native metabolite was analyzed by direct probe mass spectrometry. This analysis was consistent with a hydroxyl in the 24 position, and was also consistent with the GC-MS analysis of the TMS-derivative described above. The native metabolite showed the expected molecular ion at m/z 428 and a distinctive fragment at m/z 367, indicating the loss of one water and the $C_{25}$–$C_{26}$–$C_{27}$ fragment of 43 mass units.

EXAMPLE 2

Synthesis of 1α,24(S)-dihydroxyvitamin $D_2$ (22E)-5,7,22-ergostatriene-3β-yl acetate (2)

To a solution of 50 gm (0.13 mol) of ergosterol (1) in 300 mL of anhydrous pyridine was added 33.3 mL (0.35 mol) of acetic anhydride. The mixture was stirred at room temperature overnight and then 600 mL of water was added. The precipitate was filtered and washed three times with 200 mL portions of acetonitrile and then air dried to yield 42.0 g (74%) of (2).

22-oxo-5α,8α-(4-phenyl-3,5-dioxo-1,2,4-triazolidine-1.2-diyl)23,24-dinor-6-cholene-3β-yl acetate (4)

To a solution of 33.0 g (0.075 mol) of ergosterol acetate (2) in 1000 mL of chloroform was added 13.2 g (0.075 mol) of 4-phenyl-1,2,4-triazoline-3,5-dione. The solution of the thus formed (3) was stirred at room temperature for 30 min. and then 5 ml of pyridine was added. The solution was cooled to −78° C. and treated at −78° C. with an ozone-oxygen mixture for 2 hours and then thoroughly purged with nitrogen. Then 50 mL of dimethylsulfoxide was added and the mixture was washed with 300 mL of water, then twice with 200 ml of 2N HCl and finally 300 ml of water. The organic layer was separated, dried over anhydrous $MgSO_4$ and concentrated to dryness in vacuo. The residue was purified on a silica gel column using 30% ethyl acetate in hexane to yield 16.0 g (39%) of the title compound as a foamy solid.

$^1$H NMR: (400 MHz; $CDCl_3$): δppm 0.85 (3H, s, 18-$CH_3$), 1.10 (3H, s, 19-$CH_3$), 1.15 (3H, d, 21-$CH_3$), 1.99 (3H, s, 3β-$CH_3CO$), 5.45 (1H, m, 3α-H), 6.26 (1H, d. 7H), 6.40 (1H, d, 6-H), 7.42 (5H, m, Ph), 9.58 (1H, d, HCO).

(22E)5α,8α-(4-phenyl-3,5-dioxo-1,2,4-triazolidine-1,2-diyl)cholesta-6,22-diene-24-one-3β-yl acetate (5)

Butyllithium (1.6M solution in hexane 8.94 mL, 0.014 mol) was added to a stirred, cooled (0° C.) solution of diisopropylamine (1.45 g, 0.014 mol) in dry tetrahydrofuran (20 mL) under nitrogen. 3-Methylbutan-2-one (1.23 g, 0.014 mol) in dry tetrahydrofuran (6 mL) was added dropwise at 0° C. over 15 min. The solution was stirred at 0° C. for 1 hr. more, then cooled to −70° C. and a solution of the aldehyde (4) (6.0 g, 0.011 mol) in dry tetrahydrofuran (60 mL) was added. The temperature was raised to −20° C. and kept at this temperature for 3 hrs. Then glacial acetic acid (20 mL) was added at −20° C. and the solution was brought to room temperature. Ether (800 mL) and water (400 mL) were added and the organic layer was separated and washed with 10% hydrochloric acid (2×300 mL), saturated sodium bicarbonate solution (2×300 mL), and water (2×300 mL). Concentration gave the crude product (7.5 g) which was dissolved in tetrahydrofuran (100 mL) containing 1.5 N-hydrochloric acid (12 mL). After refluxing for 1.5 hrs., the mixture was diluted with ether (600 mL), washed with a 5% sodium carbonate solution (2×200 mL) and water (2×200 mL), and dried (anhydrous $MgSO_4$). Concentration under reduced pressure gave the crude product (7.0 g). Chromatography over silica gel (50% ethyl cetate in hexane) gave the enone (5) 4.0 g (59%).

$^1$H NMR: (400 MHz): δppm 0.83 (3H, s. 18-$CH_3$), 0.99 (3H, s, 19-$CH_3$), 1.09 (6H, dd, 26 and 27-$CH_3$), 1.12 (3H, d, 21-$CH_3$), 2.0 (3H, s, 3β-$CH_3CO$), 2.84 (1H, m, 25-H), 5.45 (1H, m, 3α-H), 6.06 (1H, d, 23-H), 6.24 (1H, d, 7-H), 6.39 (1H, d, 6-H), 6.71 (1H, dd, 22-H), 7.42 (5H, m, Ph).

(22E)-5α,8α-(4-phenyl-3,5-dioxo-1,2,4-triazolidine- 1,2-diyl)-6,22-ergostadiene-3β,24-diol (6)

The enone (5) (3.5 g, 5.7 mmol) in dry ether (100 mL) was cooled to 0° C. and methylmagnesium bromide (3.0 M solution in ether 6.8 mL, 0.02 mol) was added dropwise. After 1 hr. at 0° C., saturated ammonium chloride (100 mL) was added. The organic layer was separated. The aqueous layer was extracted with ether (2×200 mL). The combined ether phases were dried over anhydrous $MgSO_4$ and concentrated to dryness in vacuo to yield the crude product 3.0 g (90%) of (6).

(22E)-5,7,22-ergostatriene-3β,24-diol (7)

To a solution of 3.0 g (5.1 mmol) of (6) in dry tetrahydrofuran (250 mL) was added 3.6 g (0.09 mol) of lithium aluminum hydride. The mixture was heated under reflux for 3 hrs., cooled with ice water bath and reaction mixture decomposed by the cautious dropwise addition of ice water (5 mL). The mixture was filtered and the filtrate was concentrated in vacuo to remove most of the tetrahydrofuran. The residue was dissolved in 200 mL of ethyl acetate and washed twice with saturated NaCl solution (2×200 mL), dried over anhydrous $MgSO_4$ and concentrated in vacuo. The residue was purified on a silica gel column using 30% ethyl acetate in hexane to yield 1.5 g (71%) of (7).

$^1$H NMR: (400 MHz, $CDCl_3$): δppm 0.64 (3H, s, 18-H), 0.88 (6H, dd, 26 and 27-$CH_3$), 0.93 (3H, s, 19-$CH_3$), 1.06 (3H, d, 21-$CH_3$), 1.19 (3H, s, 28-$CH_3$), 3.55 (1H, m, 3α-H), 5.36 (1H, d, 7-H), 5.42 (2H, m, 22 and 23-H), 5.52 (1H, d, 6-H). UV (ethanol) $\lambda_{max}$: 282 nm.

24-hydroxyvitamin $D_2$ (8)

One gram (2.4 mmol) of (2 was dissolved in 250 mL of ether and benzene (4:1) and irradiated with stirring under nitrogen in a water-cooled quartz immersion well using a Hanovia medium-pressure UV lamp for 2 hrs. The solution was concentrated in vacuo, redissolved in 100 mL of ethanol and heated under reflux overnight. The solution was concentrated to dryness in vacuo and the residue was purified on a silica gel column using 30% ethyl acetate in hexane to yield 0.55 g (55%) of (8).

$^1$H NMR: (400 MHz, $CDCl_3$): βppm 0.57 (3H, s, 18-$CH_3$), 0.92 (6H, dd, 26 and 27-$CH_3$), 1.06 (3H, d, 21-$CH_3$), 1.20 (3H, s, 28-$CH_3$), 3.93 (1H, m, 3-H), 4.79 (1H, m (sharp), 19-H), 5.01 (1H, m, (sharp), 19-H), 5.43 (2H, m, 22 and 23-H), 6.02 (1H, d, 7-H), 6.22 (1H, d, 6-H). UV (ethanol) $\lambda_{max}$: 265 nm.

24-hydroxyvitamin $D_2$ tosylate (9)

To a solution of 0.55 g (1.3 mmol) of (8) dissolved in 5 mL of anhydrous pyridine was added 0.6 g (3.2 mmol) of tosyl chloride. The mixture was stirred under nitrogen at 5° C. for 20 hrs. The reaction mixture was poured into 100 mL of cold saturated $NaHCO_3$ solution and extracted with ether (3×100 mL). The combined organic extracts were washed with 5% HCl solution (2×200 mL) saturated sodium bicarbonate solution (2×200 mL) and saturated NaCl solution (2×200 mL), dried over anhydrous $MgSO_4$ and concentrated in vacuo to yield 0.62 g (84%) of (9).

$^1$H NMR: (400 MHz, $CDCl_3$): δppm 0.57 (3H, s, 18-$CH_3$), 0.92 (6H, dd, 26 and27-$CH_3$), 1.08 (3H, d, 21-$CH_3$), 1.24 (3H, s, 28-$CH_3$), 2.43 (3H, s, $CH_3$ (tosylate), 4.69 (1H, m, 3-H), 4.77 (1H, m, (sharp), 19-H), 5.0 (1H, m, (sharp), 19-H), 5.42 (2H, m, 22 and 23-H), 6.03 (1-H, d, 7-H), 6.25 (1-H, d, 6-H) 7.31 and 7.83 (4H, d, aromatic).

24-hydroxy-3,5-cyclovitamin $D_2$ (10)

To a solution of 0.6 g (1.06 mmol) of (9) dissolved in 50 mL of anhydrous methanol was added sodium bicarbonate 4.0 g (0.047 mol). The mixture was heated at reflux for 6 hrs. The reaction mixture was concentrated in vacuo. Water (100 mL) was added followed by extraction with ether (2×200 mL). The combined ether extracts were dried over anhydrous $MgSO_4$ and concentrated to dryness in vacuo to yield 450 mg (100%) of (10) as an oil.

1α,24-dihydroxy-3,5-cyclovitamin $D_2$ (11)

Tert-butyl hydroperoxide (870 µL (2.61 mmol); 3M in toluene) was added to a suspension of 73 mg (0.66 mmol) of selenium dioxide in 50 ml of anhydrous dichloromethane under nitrogen. The mixture was stirred at room temperature under nitrogen for 3 hrs. Then 0.1 mL of anhydrous pyridine was added followed by a solution of 450 mg (1.06 mmol) of (10) dissolved in 15 ml of anhydrous dichloromethane. The mixture was stirred under nitrogen at room temperature for 10 min. then 25 mL of 10% NaOH solution was added and the mixture was extracted with ether (3×100 mL). The combined ether extracts were washed with 10% NaOH solution (2×100 mL), water (2×100 mL), saturated sodium chloride solution (2×100 mL), dried over anhydrous $MgSO_4$ and concentrated to dryness in vacuo. The residue was purified on a silica gel column using a mixture of 30% ethyl acetate in hexane to yield 110 mg (24%) of (11).

$^1$H NMR: (400 MHz, $CDCl_3$): δppm, 0.55 (3H, s, 18$CH_3$), 0.90 (6H, dd, 26 and 27-$CH_3$), 1.03 (3H, d, 21-$CH_3$), 1.19 (3H, s, 28-$CH_3$), 3.25 (3H, s, —$OCH_3$), 4.19 (1H, d, 6-H), 4.19 (1H, m, 1-H), 4.92 (2H, d, 7-H), 5.15 (1H, m, (sharp), 19-H), 5.2 (1H, m, (sharp), 19-H), 5.42 (2H, m, 22 and 23-H).

5,6-cis and 5,6-trans-1α,24-dihydroxyvitamin $D_2$ (12,13)

1α,24-dihydroxy-3,5-cyclovitamin $D_2$ (11) 110 mg (0.25 mmol) was dissolved in 2.0 mL of dimethylsulfoxide and 1.5 mL of acetic acid and heated at 50° C. under nitrogen for 1 hr. The solution was poured over ice and 50 mL of saturated $NaHCO_3$ solution. The mixture was extracted with ether (3×100 mL). The combined ether extracts were washed with saturated $NaHCO_3$ solution (3×100 mL), water (2×100 mL), saturated NaCl solution (2×200 mL), dried over anhydrous $MgSO_4$ and concentrated in vacuo to yield the crude product 100 mg (93%) of (12) and (13).

5,6-cis-1α,24-dihydroxyvitamin $D_2$ (12)

To a solution of (12) and (13) in 5 mL of ethyl acetate was added 20 mg (0.2 mmol) of maleic anhydride and the mixture was stirred at 35° C. for 24 hrs. under nitrogen. The solution was concentrated to dryness in vacuo. The residue was purified on a silica gel column using 50% ethyl acetate in hexane to yield 20 mg (22%) of (12).

$^1$H NMR: (400 MHz, $CDCl_3$): δppm 0.57 (3H, s, 18-$CH_3$), 0.89 (6H, dd, 26 and 27-$CH_3$), 1.04 (3H, d, 21-$CH_3$), 1.21 (3H, s, 28-$CH_3$), 4.23 (1H, m, 3-H), 4.40 (1H, m, 1-H), 5.0 (1H, m, (sharp), 19-H), 5.33 (1H, m, (sharp), 19-H), 5.44 (2H, m, 22 and 23-H), 6.01 (1H, d, 7-H), 6.37 (1H, d, 6-H). UV (ethanol) $\lambda_{max}$: 265 nm.

1α,24(S)-dihydroxyvitamin $D_2$ (14)

The 24 epimers of 1α,24-$(OH)_2D_2$ were separated by high pressure liquid chromatography, performed on a Waters instrument using a reverse-phase Supelco C-8 prep. column (25 cm×21.2 mm; particle size 12 µm) with the solvent system, acetonitrile:water, 60:40, 10 mL/min. The epimers were given the designations epimer 1 and epimer 2. Under these conditions the retention time of epimer 1 was 63 min., and the retention time of epimer 2 was 71 min. Using x-ray crystallography, it was determined that the stereochemistry of epimer 2 was 1α,24(R)-$(OH)_2D_2$. The stereochemistry of epimer 1 was therefore known to be 1α,24(S)-$(OH)_2D_2$

EXAMPLE 3

Figure 3:
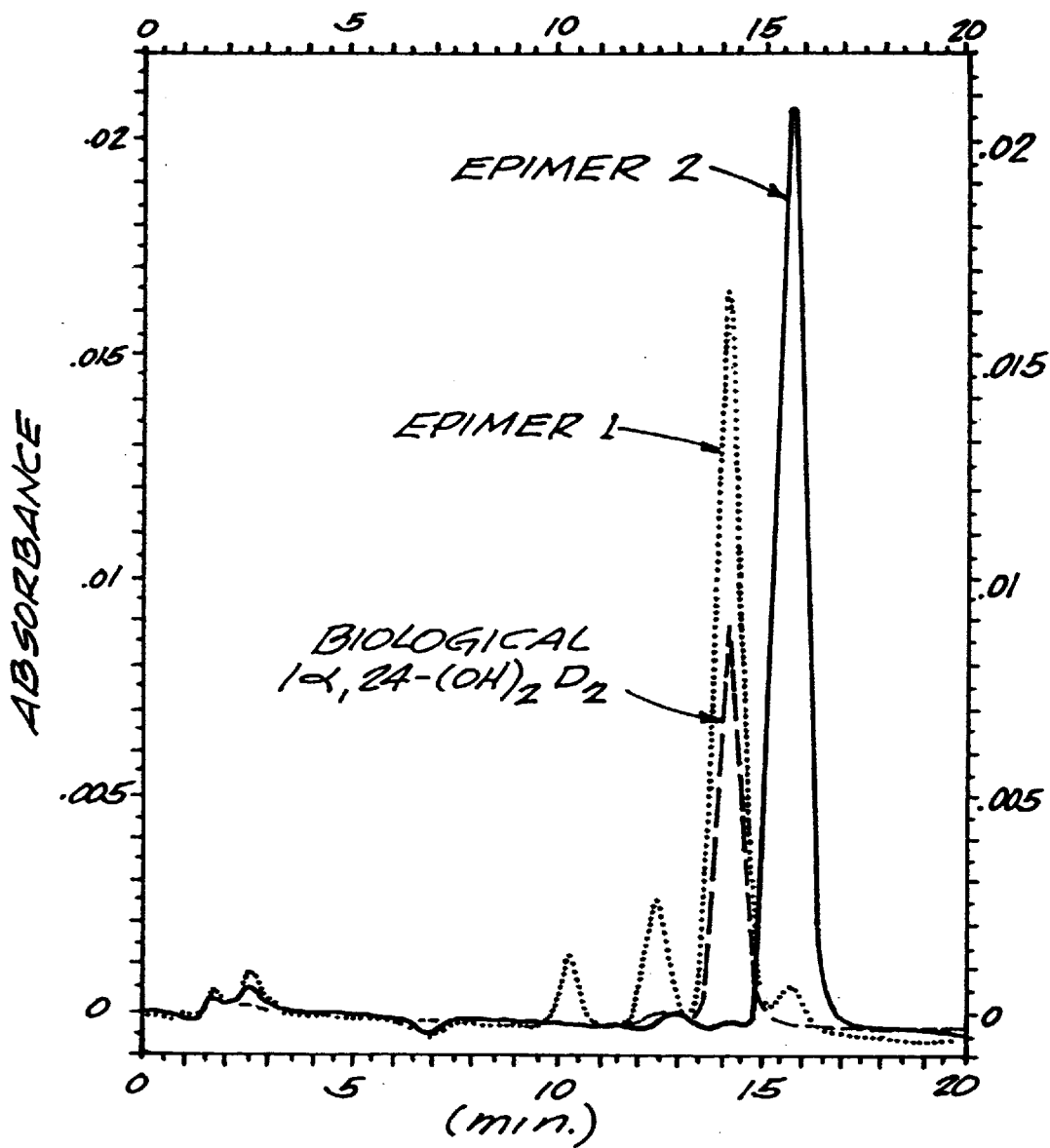
FIG. 3 is a reverse phase high pressure liquid chromatography profile of biological 1α,24-dihydroxyvitamin $D_2$ and the R and S epimers of synthetic 1α,24-dihydroxyvitamin $D_2$.

Identification of the Stereochemistry and the Biologically Derived 1α, 24(?)-$(OH)_2D_2$ Metabolite by Comparison to the Chemically Synthesized Epimers, 1α,24(S)-$(OH)_2D_2$ and 1α,24(R)-$(OH)_2D_2$ The stereochemistry of the biologically generated metabolite obtained as described in example 1, above, was compared by high pressure liquid chromatography and gas chromatography to the chemically synthesized epimers obtained as described in example 2, above. Based on these comparisons, it was determined that the biologically produced metabolite has the structure, 1α,24(S)-$(OH)_2D_2$. FIG. 3 shows a profile of the high pressure liquid chromatography experiment making this comparison. In FIG. 3, epimer 1 is the chemically synthesized 1α,24(S)-$(OH)_2D_2$.

(a) High pressure liquid chromatographic comparisons utilized two different columns and solvent systems. On the reverse-phase column Zorbax-ODS (Dupont Instruments; 3 µ; 6.2 mm×8 cm) utilizing the solvent system, acetonitrile:water, 60:40, 1 mL/min., the biological metabolite emerged at 14.3 min. and 1α,24(S)-$(OH)_2D_2$ ran at 14.2 min.; however, 1α,24(R)-$(OH)_2D_2$ ran at 15.7 min.

On the straight-phase column Zorbax-SIL (Dupont Instruments; 3 µ; 6.2 mm×8 cm) utilizing the solvent system, hexane:isopropanol:methanol, 94:5:1, 1 ml/min., the biological metabolite emerged at 22.4 min. and 1α,24(S)-$(OH)_2D_2$ ran at 22.4 min.; however, 1α,24(R)-$(OH)_2D_2$ ran at 22.8.

(b) With gas chromatography, 1α,24(S)-$(OH)_2D_2$ co-migrated with the biologically generated compound whereas the retention time of 1α,24(R)-$(OH)_2D_2$ was quite different (Table 1).

TABLE 1

Gas Chromatography Retention Times of Pyro-Derivatives Relative to Pyro-1α,25-$(OH)_2D_3$

| Compound | Relative Retention Time* |
| --- | --- |
| 1α,24(S)-$(OH)_2D_2$ | 1.0165 |
| 1α,24(R)-$(OH)_2D_2$ | 1.0098 |
| Biological Metabolite | 1.0163 |

*where the pyro-derivatives are compared retention time is expressed relative to an internal standard 1α,25-$(OH)_2D_3$.

EXAMPLE 4

Comparison of the Biological Activity of 1α,24(S)-$(OH)_2D_2$ and 1α,24(R)-$(OH)_2D_2$ The biological activity in vitro of chemically synthesized 1α,24(S)-$(OH)_2D_2$ and 1α,24(R)-$(OH)_2D_2$ was measured using a vitamin D-dependent transcriptional activation model system in which a vitamin D receptor (VDR)-expressing plasmid pSG5-hVDR1/3 and a plasmid p(CT4)$^4$TKGH containing a Growth Hormone (GH)-gene, under the control of a vitamin D-responsive element (VDRE) were co-transfected into Green monkey kidney, COS-1 cells. DNA's for these two vectors were supplied by Dr. Mark Haussler, Department of Biochemistry, University of Arizona, Tucson, Ariz.

Transfected cells were incubated with vitamin D metabolites and growth hormone production was measured. As shown in Table 2, 1α,24(S)-$(OH)_2D_2$ has significantly more activity in this system than 1α,24(R)-$(OH)_2D_2$.

TABLE 2

Vitamin D Inducible Growth Hormone Production in Transfected COS-1 Cells.

| Inducer | Molar Concentration | Vitamin D-Inducible Growth Hormone Production | |
|---|---|---|---|
| | | Total GH Production* (ng/ml) | Net vitamin D-inducible GH-production (ng/ml) |
| Ethanol | | 44 | 0 |
| 25-OH-$D_3$ | $10^{-7}$ | 245 | 201 |
| | $10^{-6}$ | 1100 | 1056 |
| | $10^{-5}$ | 775 | 731 |
| $1\alpha,25$-$(OH)_2D_3$ | $10^{-10}$ | 74 | 30 |
| | $10^{-9}$ | 925 | 881 |
| | $10^{-8}$ | 1475 | 1441 |
| $1\alpha,24(S)$-$(OH)_2D_2$ | $5 \times 10^{-10}$ | 425 | 381 |
| | $5 \times 10^{-9}$ | 1350 | 1306 |
| $1\alpha,24(R)$-$(OH)_2D_2$ | $5 \times 10^{-8}$ | 1182 | 1138 |
| | $10^{-9}$ | 80 | 36 |
| | $10^{-8}$ | 1100 | 1056 |
| | $10^{-7}$ | 1300 | 1256 |

*Averages of duplicate determinations

EXAMPLE 5

Affinity of $1\alpha,24(S)$-$(OH)_2D_2$ for the Vitamin D Receptor (VDR)

The affinity of $1\alpha,24(S)$-$(OH)2D_2$ for the mammalian vitamin D receptor (VDR) was assessed using a commercially available kit of bovine thymus VDR and standard $1,25$-$(OH)_2$-$D_3$ solutions from Incstar (Stillwater, Minn.). Purified $1\alpha,24(S)$-$(OH)_2D_2$ was quantitated by photodiode array spectrophotometry and assayed in the radioreceptor assay. The half-maximal binding of $1\alpha,24(S)$-$(OH)_2D_2$ was approximately 150 pg/mL whereas that of $1\alpha,25$-$(OH)_2D_2$ was 80 pg/mL. Thus, the $1\alpha,24(S)$-$(OH)_2D_2$ had a two-fold lower affinity for bovine thymus VDR than does $1\alpha,25$-$(OH)_2D_3$, indicating that $1\alpha,24(S)$-$(OH)_2D_2$ had potent biological activity.

EXAMPLE 6

Figure 4:
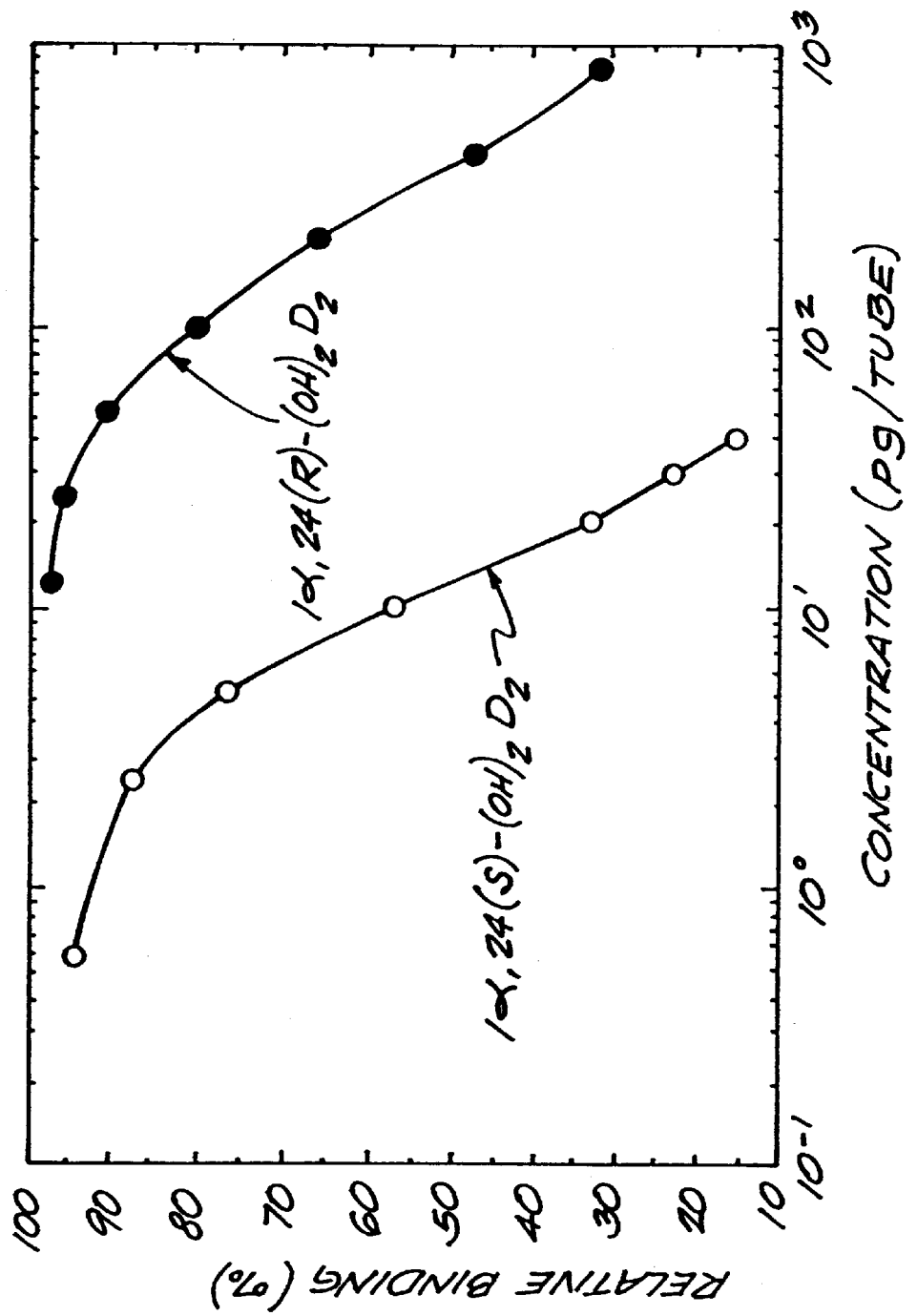
FIG. 4 is a graph illustrating the relative binding affinities of 1α,24(S)-$(OH)_2D_2$ and 1α,24(R)-$(OH)_2D_2$.

Relative Affinities of $1\alpha,24(S)$-$(OH)_2D_2$ and $1\alpha,24(R)$-$(OH)_2D_2$ for the Vitamin D Receptor The relative affinities of $1\alpha,24(R)$-$(OH)_2D_2$ and $1\alpha,24(S)$-$(OH)_2D_2$ for the vitamin D receptor (VDR) were assessed using commercially available reagents of bovine thymus VDR and standard $1\alpha,25$-$(OH)_2D_3$ solutions from Incstar (Stillwater, Minn.). The purified $1\alpha,24(R)$-$(OH)_2D_2$ and $1\alpha,24(S)$-$(OH)_2D_2$ epimers were quantitated by ultraviolet spectroscopy. The concentration of $1\alpha,24(R)$-$(OH)_2D_2$ required to produce the same displacement of $^3H$-$1\alpha,25$-$(OH)_2D_3$ tracer from the receptor was 20 to 30 times that required for $1\alpha,24(S)$-$(OH)_2D_2$, as shown in FIG. 4. These data indicate that the activity of the $1\alpha,24(S)$-$(OH)_2D_2$ epimer is significantly greater than that of the $1\alpha,24(R)$-$(OH)_2D_2$ epimer.

EXAMPLE 7

Affinity of $1\alpha,24(S)$-$(OH)_2D_2$ for the Vitamin D Serum Binding Protein (DBP)

The affinity of $1\alpha,24(S)$-$(OH)_2D_2$ for the vitamin D serum binding protein (DBP) was assessed using vitamin D deficient rat serum according to known methods in the art. The data indicated that the $1\alpha,24(S)$-$(OH)_2D_2$ binding of DBP was at least 1000 times weaker than that for 25-OH-$D_3$. Given the strong binding of $1\alpha,24(S)$-$(OH)_2D_2$ for the VDR and weak binding for the DBP, this compound would tend to be taken up by target cells, thus possessing a potent biological activity. In addition, the weak binding by the DBP was indicative of more rapid clearance, allowing for low toxicity.

Thus, the preceding assays demonstrated that the new $1\alpha,24(S)$-$(OH)_2D_2$ exhibited a distinct and unique spectrum of activities—namely, high biological potency and low toxicity which clearly distinguished the compound from those of the prior art and from its 24(R) epimer.

EXAMPLE 8

Generation of $1\alpha,24(S)$-$(OH)_2D_2$ from Vitamin $D_2$ and 24-OH-$D_2$

Vitamin $D_2$ or 24-OH-$D_2$ was administered (either oral or intraperitoneal supplementation) to vitamin D-deficient rats. Lipid extracts of the plasma were prepared and the metabolites purified by the method of Horst et al. (Horst, R. L., Koszewski, N.J. and Reinhardt, T. A., *Biochem.*, 29:578–82 (1990)) described below for synthesyzing standard biological $1\alpha,24$-$(OH)_2D_2$.

Standard biological $1\alpha,24$-$(OH)_2D_2$ was synthesized in vitro from 24-OH-$D_2$ by incubating 10 μg of 24-OH-$D_2$ in flask containing 5 mL of 20% kidney homogenates made from vitamin D-deficient chicks. The product of this reaction was isolated by HPLC and identified by mass spectrometry. In the lipid extracts of the plasma from the vitamin D-deficient rats administered vitamin $D_2$ or 24-OH-$D_2$, one metabolite isolated co-migrated on HPLC with the standard $1\alpha,24$-$(OH)_2D_2$, indicating that $1\alpha,24$-$(OH)_2D_2$ is a natural metabolite of vitamin $D_2$. In contrast, comparable rats administered vitamin $D_3$ had no detectable 24-OH-$D_3$.

EXAMPLE 9

Preferential Production of $1\alpha,24(S)$-$(OH)_2D_2$ with Increased Substrate Concentrations in vitro Hep 3B cells were incubated with $1\alpha$-OH-$D_2$, as described above, at final concentrations of 1, 10, or 100 nM (Experiment 1), and 1 or 10 μM (Experiment 2) and $1\alpha,24(S)$-$(OH)_2D_2$ was extracted and purified. The $1\alpha,24(S)$-$(OH)_2 D_2$ and $1\alpha,25$-$(OH)_2D_2$ metabolites were quantitated by recovered radiolabel (Experiment 1) or by photodiode array spectrophotometry (Experiment 2). As shown in Table 3, the amount of $1\alpha,24(S)$-$(OH)_2D_2$ increased relative to the amount of $1\alpha,25$-$(OH)_2D_2$ as the substrate concentration was raised. This indicates that in this system $1\alpha,24(S)$-$(OH)_2 D_2$ was the predominant natural active metabolite of $1\alpha$-OH-$D_2$ at higher substrate concentrations.

TABLE 3

| EXPERIMENT | SUBSTRATE CONCENTRATION | PRODUCT FORMED |
|---|---|---|
| 1 | nM | Ratio of $1\alpha,24(S)$-$(OH)_2D_2$ to $1\alpha,25$-$(OH)_2D_2$ |
| | 1 | 1:4 |
| | 10 | 1:1 |
| | 100 | 1.5:1 |

TABLE 3-continued

| EXPERIMENT | SUBSTRATE CONCENTRATION | PRODUCT FORMED | |
|---|---|---|---|
| 2 | µM | Rate of Production, pmol per $10^6$ cells/day | |
| | | $1\alpha,24(S)\text{-}(OH)_2D_2$ | $1\alpha,25\text{-}(OH)_2D_2$ |
| | 1 | 4.9 | N.D.* |
| | 10 | 59 | 7.4 |

*N.D. means not detectable

EXAMPLE 10

Production of $1\alpha,24(S)\text{-}(OH)_2D_2$ in Osteoporotic Women Administered $1\alpha\text{-}(OH)_2D_2$ An increase in the production of $1\alpha,24(S)\text{-}(OH)_2D_2$ relative to $1\alpha,25\text{-}(OH)_2D_2$ has also been observed by the present inventors in human females who received $1\alpha\text{-}OH\text{-}D_2$ as part of an investigation of that drug for the treatment of osteoporosis. Following either a single dose of 2 µg of $1\alpha\text{-}OH\text{-}D_2$ or daily doses of 8 µg/day for one week, blood was collected and analyzed for the metabolites $1\alpha,24(S)\text{-}(OH)_2D_2$ and $1\alpha,25\text{-}(OH)_2D_2$. Lipid was extracted from the blood, and the metabolites were purified by HPLC using standard methods and quantified with the radioreceptor assay produced by Incstar (Stillwater, Minn.). One day after a single 2 µg dose, the level of $1\alpha,24(S)\text{-}(OH)_2D_2$ was undetectable with the $1\alpha,25\text{-}(OH)_2D_2$ level being approximately 11 pg/ml. In contrast, one day following the last dose of 8 µg, the level of $1\alpha,24(S)\text{-}(OH)_2D_2$ averaged 9 pg/mL with the $1\alpha,25\text{-}(OH)_2D_2$ level averaging 30 pg/mL.

EXAMPLE 11

Dose Ranging Study in Postmenopausal Osteoporotic Women

Twenty postmenopausal osteoporotic women are enrolled in an open label study. The selected patients have ages between 55 and 75 years, and exhibit L2–L3 vertebral bone mineral density between 0.7 and 1.05 g/cm$^2$, as determined by measurements with a LUNAR Bone Densitometer (Lunar Corporation, Madison, Wis.).

In admission to the study, all patients receive instruction on selecting a daily diet containing 400 to 600 mg of calcium. Compliance to this diet is verified at weekly intervals by 24-hour food records and by interviews with each patient.

All patients complete a one-week baseline period, a five-week treatment period, and a one-week post-treatment observation period. During the treatment period, patients orally self-administer $1\alpha,24(S)$-dihydroxyvitamin $D_2$ at an initial dose of 0.5 µg/day for the first week, and at successively higher doses of 1.0, 2.0, 4.0, and 8.0 µg/day in each of the following four weeks. All doses are administered before breakfast.

Blood and urine chemistries are monitored on a weekly basis throughout the study. Key blood chemistries include fasting serum levels of calcium, phosphorus, osteocalcin, creatinine, and blood urea nitrogen. Key urine chemistries include 24-hour excretion of calcium, phosphorus, and creatinine.

Blood and urine data from this clinical study indicate that this compound does not adversely affect kidney function, as determined by creatinine clearance and blood levels of urea nitrogen; nor does it increase urinary excretion of hydroxyproline, indicating the absence of any stimulatory effect on bone resorption. The compound has no effect on any routinely monitored serum parameters, indicating the absence of adverse metabolic effects.

A positive effect of $1\alpha,24(S)$-dihydroxyvitamin $D_2$ on calcium homeostasis is evident from modest increases in 24-hour urinary calcium levels, confirming that the compound increases intestinal calcium absorption, and from increases in serum osteocalcin levels, indicating that the compound stimulates the osteoblasts.

EXAMPLE 12

Preventive Treatment of Bone Mass Loss in Postmenopausal Osteoporotic Women

A clinical study is conducted with postmenopausal osteoporotic out-patients having ages between 55 and 75 years. The study involves up to 120 patients randomly divided into three treatment groups and continues for 24 to 36 months. Two of the treatment groups receive constant dosages of $1\alpha,24(S)$-dihydroxyvitamin $D_2$ (u.i.d.; two different dose levels at or above 1.0 µg/day) and the other group receives a matching placebo. All patients maintain a normal intake of dietary calcium (500 to 800 mg/day) and refrain from using calcium supplements. Efficacy is evaluated by pre-and post-treatment comparisons of the patient groups with regard to (a) total body calcium retention, and (b) radial and spinal bone mineral density as determined by dual-photon absorptiometry (DPA) or dual-energy x-ray absorptiometry (DEXA). Safety is evaluated by comparisons of urinary hydroxyproline excretion, serum and urine calcium levels, creatinine clearance, blood urea nitrogen, and other routine determinations.

The results show that patients treated with $1\alpha,24(S)$-dihydroxyvitamin $D_2$ exhibit significantly higher total body calcium, and radial and spinal bone densities relative to patients treated with placebo. The monitored safety parameters confirm an insignificant incidence of hypercalcemia or hypercalciuria, or any other metabolic disturbance with $1\alpha,24(S)$-dihydroxyvitamin $D_2$ therapy.

EXAMPLE 13

Prophylaxis of Postmenopausal Bone Loss

A clinical study is conducted with healthy postmenopausal women having ages between 55 and 60 years. The study involves up to 80 patients randomly divided into two treatment groups, and continues for 24 to 36 months. One treatment group receives a constant dosage of $1\alpha,24(S)$-dihydroxyvitamin $D_2$ (u.i.d.; a dose level at or above 1.0 µg/day) and the other receives a matching placebo. The study is conducted as indicated in Example 2 above.

The results show that patients treated with $1\alpha,24(S)$-dihydroxyvitamin $D_2$ exhibit reduced losses in total body calcium, radial or spinal bone densities relative to baseline values. In contrast, patients treated with placebo show significant losses in these parameters relative to baseline values. The monitored safety parameters confirm the safety of long-term $1\alpha,24(S)$-dihydroxyvitamin $D_2$ administration at this dose level.

EXAMPLE 14

Management of Hypocalcemia and the Resultant Metabolic Bone Disease in Chronic Hemodialysis Patients A twelve-month, double-blind, placebo-controlled clinical trial is conducted with thirty men and women with renal disease who are undergoing chronic hemodialysis. All patients enter an 8-week control period during which time they receive a maintenance dose of Vitamin $D_3$ (400 IU/day). After this control period, the patients are randomized into two treatment groups: one group receives a constant dosage of $1\alpha,24(S)$-dihydroxyvitamin $D_2$ (u.i.d.; a dosage greater than 3.0 µg/day) and the other group receives a matching placebo. Both treatment groups receive a maintenance dosage of Vitamin $D_3$, maintain a normal intake of dietary calcium, and refrain from using calcium supplements. Efficacy is evaluated by pre- and post-treatment comparisons of the two patient groups with regard to (a) direct measurements of intestinal calcium absorption, (b) total body calcium retention, (c) radial and spinal bone mineral density, or (d) determinations of serum calcium. Safety is evaluated by regular monitoring of serum calcium.

Analysis of the clinical data show that $1\alpha,24(S)$-dihydroxyvitamin $D_2$ significantly increases intestinal calcium absorption, as determined by direct measurements using a double-isotope technique. Patients treated with this compound show normalized serum calcium levels, stable values for total body calcium, and stable radial and spinal bone densities relative to baseline values. In contrast, patients treated with placebo show frequent hypocalcemia, significant reductions in total body calcium and radial and spinal bone density. An insignificant incidence of hypercalcemia is observed in the treated group.

MEDICAMENT PREPARATIONS

EXAMPLE 15

A topical cream is prepared by dissolving 1.0 mg of $1\alpha,24(S)$-dihydroxyvitamin $D_2$ in 1 g of almond oil. To this solution is added 40 gm of mineral oil and 20 gm of self-emulsifying beeswax. The mixture is heated to liquefy. After the addition of 40 ml hot water, the mixture is mixed well. The resulting cream contains approximately 10 µg of $1\alpha,24(S)$-dihydroxyvitamin $D_2$ per gram of cream.

EXAMPLE 16

An ointment is prepared by dissolving 1.0 mg of $1\alpha,24$(S)-dihydroxyvitamin $D_2$ in 30 g of almond oil. To this solution is added 70 gm of white soft paraffin which had been warmed just enough to be liquefied. The ointment is mixed well and allowed to cool. This ointment contains approximately 10 µg $1\alpha,24(S)$-dihydroxyvitamin $D_2$ per gram of ointment.

EXAMPLE 17

To the ointment of Example 14 is added with thorough mixing 0.5 g of adenosine and 2.0 g of papaverine base, both dissolved in a minimum quantity of dimethyl sulfoxide. The additional ingredients are present to the extent of about 0.5 wt % (adenosine) and 2 wt % (papaverine base).

EXAMPLE 18

To the ointment of Example 14 is added with thorough mixing 10,000 U of Vitamin A dissolved in a minimum quantity of vegetable oil. The resultant ointment contains about 100 U Vitamin A per gram of the ointment.

EXAMPLE 19

A dermatological lotion is prepared by dissolving 1.0 mg of $1\alpha,24(S)$-dihydroxyvitamin $D_2$ in 100 g of dry propylene glycol. The lotion is stored in a refrigerator in a brown bottle and contains about 10 µg of $1\alpha,24(S)$-dihydroxyvitamin $D_2$ per gram of lotion.

EXAMPLE 20

In 1 g of almond oil is dissolved 0.2 mg of $1\alpha,24$-dihydroxyvitamin $D_2$. To the solution is added 40 g of mineral oil and 20 g of self-emulsifying beeswax, followed by 40 ml of hot water. The mixture is mixed well to produce a cosmetic cream containing about 2.0 µg of $1\alpha,24(S)$-dihydroxyvitamin $D_2$ per gram of cream.

EXAMPLE 21

To a cosmetic cream prepared according to example 18 is added 100 mg adenosine. The cream is mixed well and contains about 0.1 wt % adenosine.

EXAMPLE 22

An ointment is prepared by dissolving 100 µg of $1\alpha,24$(S)-dihydroxyvitamin $D_2$ in 30 g of almond oil. To the solution so produced is added 70 g white soft paraffin which had been warmed just enough to be liquefied. The ointment is mixed well and allowed to cool. The ointment so produced contains about 1.0 µg of $1\alpha,24$-dihydroxyvitamin $D_2$ per gram of ointment.

EXAMPLE 23

To the cosmetic ointment of Example 18 is added with thorough mixing 200 U/g Vitamin A dissolved in a minimum amount of vegetable oil.

EXAMPLE 24

A cosmetic lotion is prepared by dissolving 300 µg of $1\alpha,24$-dihydroxyvitamin D2 in 100 g of dry propylene glycol. The lotion is stored in a refrigerator in a brown bottle and contains about 3.0 µg $1\alpha,24(S)$-dihydroxyvitamin $D_2$ per gram of lotion.

EXAMPLE 25

Dermatological Testing

Compositions containing $1\alpha,24(S)$-dihydroxyvitamin $D_2$ are evaluated for therapeutic efficacy of the composition in the topical treatment of dermatitis (contact and ectopic). The composition evaluated is an ointment containing 10 µg of $1\alpha,24$-dihydroxyvitamin $D_2$ per gram of ointment in a petrolatum-almond oil base. The control composition is identical except that it does not contain the active agent $1\alpha,24(S)$-dihydroxyvitamin $D_2$. The patients are treated in an out-patient clinic. They are instructed to use the preparation two times a day.

The ointment is as far as possible applied to a single lesion, or to an area of the disease. The ointment and its container are weighed before the treatment starts and returned with any unused contents for reweighing at the end of the treatment.

The area of the lesion treated is estimated and recorded, and the lesion is photographed as required, together with suitable "control" lesions. The latter are preferably lesions of similar size and stage of development, either in the vicinity of the treated lesion or symmetrically contralateral. Relevant details of the photographic procedure are recorded so as to be reproduced when the lesions are next photographed (distance, aperture, angle, background, etc.). The ointment is applied twice daily and preferably left uncovered. The "control" lesions are left untreated, but if this is not possible, the treatment used on them is noted.

Evaluations of erythema, scaling, and thickness are conducted at weekly intervals by a physician, with the severity of the lesion rated from 0 to 3. The final evaluation is usually carried out at the end of four to six weeks of treatment. Those lesions treated with $1\alpha,24(S)\text{-}(OH)_2D_2$ have lower scores than the control lesions. An insignificant incidence of hypercalcemia is also observed.

EXAMPLE 26

Epidermal Cell Differentiation and Proliferation Testing

Human keratinocytes are cultured according to known modifications of the system originally described by Rheinwald and Green (*Cell*, vol.6, p.331 (1975)). The $1\alpha,24(S)$-dihydroxyvitamin $D_2$, dissolved in ethanol, is added to cells to yield a variety of concentrations between 0.05 and 5 µg/ml with the ethanol concentration not to exceed 0.5% v/v. Control cultures are supplemented with ethanol at a final concentration of 0.5% v/v. Differentiation and proliferation of epidermal cells in culture is examined by:

1. quantitation of cornified envelopes;
2. quantitation of cell density of cells attached to disks;
3. monitoring transglutaminase activity; or
4. monitoring DNA synthesis by incorporation of $^3$H-thymidine.

Cultures incubated with $1\alpha,24(S)$-dihydroxyvitamin $D_2$ have more cornified envelopes, fewer attached cells, higher transglutaminase activity, and lower DNA synthesis than control cultures.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

EXAMPLE 27

Activity of $1\alpha,24(S)\text{-}(OH)_2D_2$ in HL-60 Cell Differentiation Assay A dose-response study is conducted with $1\alpha,24(S)\text{-}(OH)_2D_2$ in the HL-60 cell differentiation assay as described by DeLuca and Ostrom (DeLuca, H. F. and Ostrem, V. K., *Prog. Clin. Biol. Res.*, vol. 259, pp. 41–55 (1988)). In this study, $1\alpha,25\text{-}(OH)_2D_3$ is used as a positive control and appropriate solvents are used as negative controls. The following variables are evaluated: nonspecific acid esterase activity, nitroblue tetrazolium (NBT) reduction, and thymidine incorporation. The results show that $1\alpha,24(S)\text{-}(OH)2D_2$ has potent activity in promoting differentiation of HL-60 promyelocytes to monocytes.

EXAMPLE 28

Antiproliferative Activity of $1\alpha,24(S)\text{-}(OH)_2D_2$ in Human Cancer Cell Lines Dose-response studies are conducted with $1\alpha,24(S)\text{-}(OH)_2D_2$ in a battery of human cancer cell lines. These cell lines include, but are not limited to, the following: BCA-1 or ZR-75-1 (breast) and COL-1 (colon), as described by Shieh, H. L. et al. *Chem. Biol. Interact.*, vol. 81, pp. 35–55 (1982). In this study, appropriate solvents are used as negative controls. The results show that $1\alpha,24(S)\text{-}(OH)_2D_2$ has potent (and reversible) antiproliferative activity, as judged by inhibition of thymidine incorporation.

EXAMPLE 29

Chemical Stability Testing

Samples of approximately 5 mg of either crystalline or powdered $1\alpha,24$-dihydroxyvitamin $D_2$ were each placed in a 5 mL volumetric flask. The flasks were exposed to identical environmental conditions of variations in heat and light. Heat and light are environmental parameters well-known to affect negatively the integrity of vitamin D compounds.

After one week's time, the contents of the flasks were visually inspected. The powdered specimen appeared to be slightly yellow in color compared to the crystalline specimen. Five mL of ethanol was added to each sample and each specimen was dissolved. These solutions were analyzed for ultraviolet absorbence from 200 to 320 nm. A reference standard $1\alpha,24$-dihydroxyvitamin $D_2$ dissolved in ethanol at the same concentration and stored in a freezer for the identical time period was similarly analyzed.

The reference standard $1\alpha,24$-dihydroxyvitamin $D_2$ exhibited an ultraviolet spectrum diagnostic for the triene functional group of the vitamin D structure, i.e., a $\lambda_{max}$ of 265 nm and $\lambda_{min}$ of 228 nm. The crystalline specimen retained the characteristic $\lambda_{max}$ of 265 nm and $\lambda_{min}$ 228 nm. In contrast, the powdered specimen has a $\lambda_{max}$ of 255 nm and $\lambda_{min}$ of 228 nm, indicating that conversion to another entity(ies) had occurred. The absorbence at 265 nm is linear with concentration according to Beer§s Law. The reference standard retained 100% of the absorbence, and therefore, 100% of its concentration. The crystalline specimen exposed to heat and light retained 93% of the absorbence. In contrast, the powdered specimen retained only 45% of the original absorbence/concentration.

The ethanol solutions of the crystalline and powdered $1\alpha,24$-dihydroxyvitamin $D_2$ were also analyzed by high performance liquid chromatography (HPLC) under the following conditions:

| | |
|---|---|
| NovaPak C18 column: | 3.9 mm × 15 cm |
| Mobile Phase: | 50:50 water:acetonitrile |
| Flow Rate: | 0.5 mL/min |
| Detection: | Photo diode array at 265 nm |
| Psi: | 1310 |
| Injection Volume: | 10 µL |

The HPLC trace of the reference standard and the crystalline $1\alpha,24$-dihydroxyvitamin $D_2$ were identical, with 96% of the UV absorbing material of the standard being $1\alpha,24$-dihydroxyvitamin $D_2$ and 95% of the crystalline material being $1\alpha,24$-dihydroxyvitamin $D_2$. These data demonstrate that after subjecting crystalline $1\alpha,24$-dihydroxyvitamin $D_2$ to heat and light over 88% of the compound remained intact.

The HPLC analysis of the powdered $1\alpha,24$-dihydroxyvitamin $D_2$, on the other hand, indicted that only 78% of the UV absorbing material was $1\alpha,24$-dihydroxyvitamin $D_2$, for an overall retention of only 35% of the compound. A weight-based normalization of the peak area for $1\alpha,24$-dihydroxyvitamin $D_2$ in the HPLC traces indicated that 100% retention of the structure of the reference standard, 93% of the crystalline specimen and 23% of the powdered specimen. Two HPLC peaks with retention times less than that of the 1α,24-dihydroxyvitamin $D_2$ appeared with the powdered specimen, but not with the reference or the crystalline specimen.

These data demonstrate the surprising stability of the environmentally exposed crystalline 1α,24-dihydroxyvitamin $D_2$ compared to powdered 1α,24-dihydroxyvitamin $D_2$.

EXAMPLE 30

Vitamin D Receptor Binding Assays of Crystalline Versus White Powder Form of 1α,24-$(OH)_2D_2$ The binding affinities of the environmentally exposed compounds, crystalline 1α,24-dihydroxyvitamin $D_2$ and powdered 1α,24-dihydroxyvitamin $D_2$, to the vitamin D receptor (VDR) were assessed using methods known in the art, as described, e.g., in Example 6. It was found that the binding affinity of crystalline 1α,24-dihydroxyvitamin $D_2$ is approximately the same as that of a reference standard 1α,24-dihydroxyvitamin $D_2$ while the powdered form was considerably less. The percent bound versus amount of compound in pg/tube are graphed in FIG. 5.

As seen in FIG. 5, the concentration of crystalline 1α,24-dihydroxyvitamin $D_2$ required to produce the same displacement of $^3$H-1α,25-dihydroxyvitamin $D_3$ tracer from the receptor was virtually the same as that required for standard 1α,24-dihydroxyvitamin $D_2$, while the powder form exposed to the same conditions has less than 25%. The $ED_{50}$ (amount of material to displace 50% of the bound $^3$H-1α,25-dihydroxyvitamin $D_3$) for the standard and the crystalline material is about 10 pg/tube; the $ED_{50}$ for the powdered material is about 40 pg/tube. These data demonstrate that the powdered form, exposed to environmental conditions, has significantly lower biological activity. In other words, the crystalline form retains more biologically active material after environmental exposure than the white powder form.

EXAMPLE 31

Inhibition of Cell Proliferation

Inhibition of cell proliferation is demonstrated using the techniques of Skowronski et al., 132 *Endocrinology* (1993) 1952–1960 and 136 *Endocrinology* (1995) 20–26, both of which are incorporated herein by reference. The cell lines, LNCAP and PC-3, which are derived from human prostate adenocarcinoma, are seeded in six-well tissue culture plates at a density of about 50,000 cells/plate. After the cells have attached and stabilized, about 2–3 days, the medium is replenished with medium containing vehicle or the active vitamin D analogue 1α,24-$(OH)_2D_2$, at concentrations from $10^{-11}$ M to $10^{-7}$ M. Medium containing test analogue or vehicle is replaced every three days. After 6–7 days, the medium is removed, the cells are rinsed, precipitated with cold 5% trichloroacetic acid, and washed with cold ethanol. The cells are solubilized with 0.2 N sodium hydroxide, and the amount of DNA determined by standard procedures. The results show that cultures incubated with 1α,24-$(OH)_2D_2$ in accordance with the present invention have significantly fewer cells than the control cultures.

EXAMPLE 32

Cell Differentiation

Using the techniques of Skowronski et al., 132 *Endocrinology* (1993) 1952–1960 and 136 *Endocrinology* (1995) 20–26, both of which are incorporated herein by reference, cells of the cell line, LNCaP, which is derived from a human metastatic prostate adenocarcinoma and known to express PSA, are seeded in six-well tissue culture plates at a density of about 50,000 cells/plate. After the cells have attached and stabilized, about 2–3 days, the medium is replenished with medium containing vehicle or the active vitamin D analogue, 1α,24-$(OH)_2D_2$, at concentrations from $10^{-11}$ M to $10^{-7}$ M. After 6–7 days, medium is removed and stored at −20° C. for prostate specific antigen (PSA) analysis.

The cells from parallel cultures are rinsed, precipitated, and the amount of DNA determined by standard procedures. PSA is measured by standard known methods. Cultures incubated with 1α,24-$(OH)_2D_2$ have significantly more PSA than control cultures when expressed as mass of PSA/cell.

EXAMPLE 33

General Treatment of Cancers

Patients with a known vitamin D receptor positive tumor (e.g., adenocarcinoma of the prostate, breast, lung, colon or pancreas, or transitional cell carcinoma of the bladder, or melanoma) participate in an open-label study of 1α,24(S)-$(OH)_2D_2$. Patients are placed on a reduced calcium diet prior to treatment, to help minimize intestinal absorption and allow ever higher doses of 1α,24(S)-dihydroxyvitamin $D_2$. This reduced calcium diet may be continued for the duration of treatment, and for one week after the last dose of the 1α,24(S)-dihydroxyvitamin $D_2$. The diet ideally restricts daily calcium intake to 400–500 mg. Patients also discontinue use of any vitamin supplements or vitamin D replacement therapies. Each patient is also asked to drink 4–6 cups of fluid more than usual intake to assure adequate oral hydration.

Each subject is monitored at regular intervals for: (1) hypercalcemia, hyperphosphatemia, hypercalciuria, hyperphosphaturia and other toxicity; (2) evidence of changes in the progression of metastatic disease; and (3) compliance with the prescribed test drug dosage.

The dosing regimen is typically on a daily dose basis of 10 μg or 20 μg per day to about 100 μg/day for 24 months. Alternatively, a non-daily dosing regimen can be used, e.g., 40 μg given every other day, 100 μg given once a week. The route of administration can vary from oral to intravenous to regional delivery (e.g., arterial infusion, via the portal vein). Oral is, of course, the easiest and most cost effective route. Regional delivery permits high dosing and generally avoids any production of hypercalcemia. Although, in the case of the compound of the present invention, the compound is substantially hypocalcemic.

After 18 months of treatment, CAT, scans, X-rays and bone scans used for evaluating the progress of metastatic disease or partial remission in many patients treated at the lower dosage, and stable disease and partial or complete remission in many patients treated at the higher dosage.

EXAMPLE 34

Treatment of Prostate Cancer

Patients with advanced androgen-independent prostate cancer participate in an open- labeled study of 1α,24-$(OH)_2D_2$. Qualified patients are at least 40 years old, exhibit histologic evidence of adenocarcinoma of the prostate, and present with progressive disease which had previously responded to hormonal intervention(s). On admission to the study, patients begin a course of therapy with oral 1α,24-

$(OH)_2D_2$ lasting 26 weeks, while discontinuing any previous use of calcium supplements, vitamin D supplements, and vitamin D hormone replacement therapies. During treatment, the patients are monitored at regular intervals for: (1) hypercalcemia, hyperphosphatemia, hypercalciuria, hyperphosphaturia and other toxicity; (2) evidence of changes in the progression of metastatic disease; and (3) compliance with the prescribed test drug dosage.

The study is conducted in two phases. During the first phase, the maximal tolerated dosage (MTD) of daily oral $1\alpha,24\text{-}(OH)_2D_2$ is determined by administering progressively higher dosages to successive groups of patients. All doses are administered in the morning before breakfast. The first group of patients is treated with 25.0 μg/day of $1\alpha,24\text{-}(OH)_2D_2$. Subsequent groups of patients are treated with 50.0, 75.0 and 100.0 μg/day. Dosing is continued uninterrupted for the duration of the study unless serum calcium exceeds 11.6 mg/dL, or other toxicity of grade 3 or 4 (NCI Common Toxicity Criteria) is observed, in which case dosing is held in abeyance until resolution of the observed toxic effect(s) and then resumed at a level which has been decreased by 10.0 μg.

Results from the first phase of the study show that the MTD for $1\alpha,24\text{-}(OH)_2D_2$ is above 20.0 μg/day, a level which is 10- to 40-fold higher than can be achieved with $1\alpha,25\text{-}(OH)_2D_3$. Analysis of blood samples collected at regular intervals from the participating patients reveal that the levels of circulating $1\alpha,24\text{-}(OH)_2D_2$ increase proportionately with the dosage administered, rising to maximum levels well above 100 pg/mL at the highest dosages, and that circulating levels of $1\alpha,25\text{-}(OH)_2D_3$ are suppressed, often to undetectable levels. Serum and urine calcium are elevated in a dose responsive manner. Patients treated with the MTD of $1\alpha,24\text{-}(OH)_2D_2$ for at least six months report that bone pain associated with metastatic disease is significantly diminished.

During the second phase, patients are treated with $1\alpha,24\text{-}(OH)_2D_2$ for 24 months at 0.5 and 1.0 times the MTD. After one and two years of treatment, CAT scans, X-rays and bone scans used for evaluating the progression of metastatic disease show stable disease or partial remission in many patients treated at the lower dosage, and stable disease and partial or complete remission in many patients treated at the higher dosage.

EXAMPLE 35

Treatment of Melanoma

The methods of Examples 33 and 34 are used to treat patients with metastatic malignant melanoma of, e.g., the jaw. After 18 months of treatment, the progress of the metastatic disease shows stable disease or partial remission.

EXAMPLE 36

Treatment of Retinoblastoma

The methods of Examples 33 and 34 is used to treat patients with metastatic retinoblastoma. After 18 months of treatment, the progress of the metastatic disease shows stable disease or partial remission.

EXAMPLE 37

Treatment of Liver Cancer

The methods of Examples 33 and 34 are used to treat patients with hepatoma. The regional delivery of the compound in accordance with the present invention, i.e., via arterial infusion, is used. After 18 months of treatment, the progress of the metastatic disease shows stable disease or partial remission.

What is claimed is:

1. A method of inhibiting hyperproliferation of malignant or neoplastic cells, comprising treating the cells with an antiproliferative amount of $1\alpha,24(S)$-dihydroxyvitamin $D_2$, the cells being associated with cancers of the lung, neck and head, pancreas, endometrium, bladder, cervix, ovaries, and liver, squamous cell carcinoma, myeloid and lymphocytic leukemia, lymphoma, medullary thyroid carcinoma, melanoma, multiple myeloma, retinoblastoma or sarcomas of the soft tissues and bone.

2. The method of claim 1, wherein the cells are cancers of the lung.

3. The method of claim 1, wherein the cells are cancers of the neck and head.

4. The method of claim 1, wherein the cells are cancers of the pancreas.

5. The method of claim 1, wherein the cells are cancers of the endometrium.

6. The method of claim 1, wherein the cells are cancers of the bladder.

7. The method of claim 1, wherein the cells are cancers of the cervix.

8. The method of claim 1, wherein the cells are cancers of the ovaries.

9. The method of claim 1, wherein the cells are cancers of the liver.

10. The method of claim 1, wherein the cells are cancers of squamous cell carcinoma.

11. The method of claim 1, wherein the cells are cancers of myeloid and lymphocytic leukemia.

12. The method of claim 1, wherein the cells are cancers of lymphoma.

13. The method of claim 1, wherein the cells are cancers of medullary thyroid carcinoma.

14. The method of claim 1, wherein the cells are cancers of melanoma.

15. The method of claim 1, wherein the cells are cancers of multiple myeloma.

16. The method of claim 1, wherein the cells are cancers of retinoblastoma or sarcomas of the soft tissues and bone.

17. A method of inhibiting the hyperproliferative activity of malignant or neoplastic cells, comprising administering to a patient suffering therefrom, an antiproliferative amount of $1\alpha,24(S)$-dihydroxyvitamin $D_2$, the cells being associated with cancers of the lung, neck and head, pancreas, endometrium, bladder, cervix, ovaries, and liver, squamous cell carcinoma, myeloid and lymphocytic leukemia, lymphoma, medullary thyroid carcinoma, melanoma, multiple myeloma, retinoblastoma or sarcomas of the soft tissues and bone.

18. A method in accordance with claim 17, wherein $1\alpha,24(S)$-dihydroxyvitamin $D_2$ is administered in a daily dosing regimen or an episodic dosing regimen.

19. A method in accordance with claim 18, wherein the episodic regimen is a dose of once every 2 to 7 days.

20. A method in accordance with claim 19, wherein the $1\alpha,24(S)$-dihydroxyvitamin $D_2$ is administered at a dose of about 10 to 200 μg/dose.

21. A method in accordance with claim 18, wherein the $1\alpha,24(S)$-dihydroxyvitamin $D_2$ is administered daily at a dose of about 10 to 100 μg/day.

22. A method in accordance with claim 18, wherein the $1\alpha,24(S)$-dihydroxyvitamin $D_2$ is administered in an episodic regimen.

23. A method in accordance with claim 22, wherein the 1α,24(S)-dihydroxyvitamin D$_2$ is administered at a dose of about 10 to 200 µg/dose.

24. A method in accordance with claim 17, wherein the 1α,24(S)-dihydroxyvitamin D$_2$ is administered orally, is administered intravenously, is directly injected into a cancer site or is regionally delivered to a cancer site.

25. A method in accordance with claim 24, wherein the 1α,24(S)-dihydroxyvitamin D$_2$ is administered orally.

26. A method in accordance with claim 17, wherein the 1α,24(S)-dihydroxyvitamin D$_2$ is co-administered with a cytotoxic agent.

27. A method in accordance with claim 26, wherein the cytotoxic agent is an antimetabolite, an antimicrotubule agent, an alkylating agent, a platinum agent, an anthracycline, a topoisomase inhibitor, or an antibiotic.

28. A method in accordance with claim 27 wherein the cytotoxic agent is estramustine phosphate or prednimustine.

29. A method in accordance with claim 27, wherein the cytotoxic agent is an antimetabolite.

30. A method in accordance with claim 29, wherein the antimetabolite in 5-fluoro-uracil, methotrexate or fludarabine.

31. A method in accordance with claim 27, wherein the cytotoxic agent is an antimicrotubule agent.

32. A method in accordance with claim 31, wherein the antimicrotubule agent is vincristine, vinblastine or a taxane.

33. A method in accordance with claim 32, wherein the taxane is paclitaxel or docetaxel.

34. A method in accordance with claim 27, wherein the cytotoxic agent is an alkylating agent.

35. A method in accordance with claim 34, wherein the alkylating agent is cyclophasphamide, melphalan, biochoroethylnitrosurea or hydroxyurea.

36. A method in accordance with claim 27, wherein the cytotoxic agent is a platinum agent.

37. A method in accordance with claim 36, wherein the platinum agent is cisplatin, carboplatin, oxaliplatin, JM-216 or CI-973.

38. A method in accordance with claim 27, wherein the cytotoxic agent is an anthracycline.

39. A method in accordance with claim 38, wherein the anthracycline is doxrubicin or daunorubicin.

40. A method in accordance with claim 27, wherein the cytotoxic agent is a topoisomase inhibitor.

41. A method in accordance with claim 40, wherein the topoisomerase inhibitor is etoposide or camptothecins.

42. A method in accordance with claim 27, wherein the cytotoxic agent is an antibiotic.

43. A method in accordance with claim 42, wherein the antibiotic is mitomycin, idarubicin, adriamycin or daunomycin.

44. A method in accordance with claim 26, wherein antiproliferative effective amount of the cytotoxic agent is lower than the antiproliferative effective amount of the cytotoxic agent when administered alone.

45. A method in accordance with claim 17, wherein the hyperproliferative activity is due to liver cancer.

46. A method in accordance with claim 17, wherein the hyperproliferative activity is due to retinoblastoma.

47. The method of claim 17, wherein the cells are cancers of the lung.

48. The method of claim 17, wherein the cells are cancers of the neck and head.

49. The method of claim 17, wherein the cells are cancers of the pancreas.

50. The method of claim 17, wherein the cells are cancers of the endometrium.

51. The method of claim 17, wherein the cells are cancers of the bladder.

52. The method of claim 17, wherein the cells are cancers of the cervix.

53. The method of claim 17, wherein the cells are cancers of the ovaries.

54. The method of claim 17, wherein the cells are cancers of the liver.

55. The method of claim 17, wherein the cells are cancers of squamous cell carcinoma.

56. The method of claim 17, wherein the cells are cancers of myeloid and lymphocytic leukemia.

57. The method of claim 17, wherein the cells are cancers of lymphoma.

58. The method of claim 17, wherein the cells are cancers of medullary thyroid carcinoma.

59. The method of claim 17, wherein the cells are cancers of melanoma.

60. The method of claim 17, wherein the cells are cancers of multiple myeloma.

61. The method of claim 17, wherein the cells are cancers of retinoblastoma or sarcomas of the soft tissues and bone.

62. A method of treating a human to alleviate the pathological effects of pancreatic cancer, endometrial cancer, small cell and non-small cell cancer of the lung (including squamous, adneocarcinoma and large cell types), squamous cell of the head and neck, bladder, ovarian and cervical cancers, myeloid and lymphocyltic leukemia, lymphoma, hepatic tumors, medullary thyroid carcinoma, multiple myeloma, melanoma, retinoblastoma or sarcomas of the soft tissue and bone, comprising administering to the human an effective amount of 1α,24(S)-dihydroxyvitamin D$_2$.

63. The method of claim 62, wherein the pathological effects are due to pancreatic cancer.

64. The method of claim 62, wherein the pathological effects are due to endometrial cancer.

65. The method of claim 62, wherein the pathological effects are due to small cell cancer of the lung.

66. The method of claim 62, wherein the pathological effects are due to large cell cancer of the lung.

67. The method of claim 62, wherein the pathological effects are due to squamous cell cancer of the head and neck.

68. The method of claim 62, wherein the pathological effects are due to bladder cancer.

69. The method of claim 62, wherein the pathological effects are due to ovarian cancer.

70. The method of claim 62, wherein the pathological effects are due to cervical cancer.

71. The method of claim 62, wherein the pathological effects are due to myeloid and lymphocyltic leukemia.

72. The method of claim 62, wherein the pathological effects are due to lymphoma.

73. The method of claim 62, wherein the pathological effects are due to hepatic tumors.

74. The method of claim 62, wherein the pathological effects are due to medullary thyroid carcinoma.

75. The method of claim 62, wherein the pathological effects are due to multiple myeloma.

76. The method of claim 62, wherein the pathological effects are due to melanoma.

77. The method of claim 62, wherein the pathological effects are due to retinoblastoma or sarcomas of the soft tissue and bone.

78. A method of enhancing the antiproliferative effect of a cytotoxic agent in a patient with a disease in need of treatment with a cytotoxic agent, comprising administering to the patient 1α,24(S)-dihydroxyvitamin D$_2$ and the cytotoxic agent.

79. A method in accordance with claim 78, wherein the 1α,24(S)-dihydroxyvitamin $D_2$ is administered from 0.5 to 7 days prior to administration of the cytotoxic agent.

80. A method in accordance with claim 79, wherein the 1α,24(S)-dihydroxyvitamin $D_2$ is administered 2 to 4 days prior to administration of the cytotoxic agent.

81. A method of inducing differentiation in malignant or neoplastic cells, comprising treating the cells with a prodifferentiative amount of 1α,24(S)-dihydroxyvitamin $D_2$.

82. A method of treating in a subject a tumor that expresses a vitamin D receptor, comprising administering to the subject an effective amount of 1α,24(S)-dihydroxyvitamin $D_2$ to raise a blood level of vitamin D to a sufficiently supraphysiologic level for a sufficient period of time to inhibit growth of the tumor, without inducing hypercalcemia in the subject.

* * * * *

UNITED STATES PATENT AND TRADEMARK OFFICE
CERTIFICATE OF CORRECTION

PATENT NO. : 6,538,037 B2
DATED : March 25, 2003
INVENTOR(S) : Charles W. Bishop et al.

It is certified that error appears in the above-identified patent and that said Letters Patent is hereby corrected as shown below:

<u>Title page,</u>
Item [56], References Cited, OTHER PUBLICATIONS, "Reddy et al." reference, insert -- Biochemistry -- before "vol. 29…"; insert -- Ishizuka et al. Steroids, vol. 37, No. 1, pp.2715 (1981). --;
Item [57], ABSTRACT,
Line 4, delete "cyotoxic" and insert -- cytoxic --;
Line 5, delete "angents" and insert -- agents --;

<u>Column 6,</u>
Line 19, delete "haracteristic" and insert -- characteristic --;
Line 21, delete "utritional" and insert -- nutritional --;
Line 35, delete "lymphocyltic" and insert -- lymphocytic --;
Line 47, delete "does" and insert -- doses --;
Line 68, delete "an Vitamin D" and insert -- a Vitamin D --;

<u>Column 7,</u>
Line 15, delete "antiobiolitics" and insert -- antibiotics --;

<u>Column 11,</u>
Line 16, delete "(4-phyel-3,5-dioxo" and insert -- (4-phyel-3.5-dioxo --;
Line 35, delete "(1H, d. 7H)" and insert -- (1H, d, 7H) --;
Line 61, delete "cetate" and insert -- acetate --;
Line 63, delete "(3H, s. 18-CH3)" and insert -- (3H, s, 18-CH3) --;

<u>Column 12,</u>
Line 31, delete "(2" and insert -- (7) --;
Line 58, delete "and27-CH3)" and insert -- and 27-CH3 --;
Line 59, delete "(tosylate)" and insert -- (toysylate)) --;

UNITED STATES PATENT AND TRADEMARK OFFICE
CERTIFICATE OF CORRECTION

PATENT NO. : 6,538,037 B2
DATED : March 25, 2003
INVENTOR(S) : Charles W. Bishop et al.

It is certified that error appears in the above-identified patent and that said Letters Patent is hereby corrected as shown below:

<u>Column 28,</u>
Lines 28 and 50, delete "lymphocyltic" and insert -- lymphocytic --.

Signed and Sealed this

Twenty-seventh Day of September, 2005

JON W. DUDAS
*Director of the United States Patent and Trademark Office*